(12) United States Patent
Ahmed et al.

(10) Patent No.: US 12,266,213 B2
(45) Date of Patent: Apr. 1, 2025

(54) PROACTIVE CONTACT TRACING ASSOCIATED WITH SHARED HEALTH EVENTS

(71) Applicant: salesforce.com, inc., San Francisco, CA (US)

(72) Inventors: Nadeem Ahmed, Mississauga (CA); Sameer K. Bhatia, Omaha, NE (US)

(73) Assignee: Salesforce, Inc., San Francisco, CA (US)

( * ) Notice: Subject to any disclaimer, the term of this patent is extended or adjusted under 35 U.S.C. 154(b) by 944 days.

(21) Appl. No.: 16/947,388

(22) Filed: Jul. 30, 2020

(65) Prior Publication Data

US 2021/0319901 A1 Oct. 14, 2021

Related U.S. Application Data

(60) Provisional application No. 63/007,764, filed on Apr. 9, 2020.

(51) Int. Cl.
*G16H 10/00* (2018.01)
*G06F 21/32* (2013.01)
(Continued)

(52) U.S. Cl.
CPC ............ *G06V 40/166* (2022.01); *G06F 21/32* (2013.01); *G06V 40/1365* (2022.01);
(Continued)

(58) Field of Classification Search
CPC ............ G06V 40/166; G06V 40/1365; G06V 40/172; G16H 40/67; G16H 10/60;
(Continued)

(56) References Cited

U.S. PATENT DOCUMENTS 5,577,188 A 11/1996 Zhu
5,608,872 A 3/1997 Schwartz et al.
(Continued)

FOREIGN PATENT DOCUMENTS

CN 102713914 A 10/2012

OTHER PUBLICATIONS

Louigene, Samantha. Database for Medical Appointments. The College of St. Scholastica. 2014. (Year: 2104).*
(Continued)

*Primary Examiner* — Christopher L Gilligan
*Assistant Examiner* — Tristan Isaac Evans
(74) *Attorney, Agent, or Firm* — Weaver Austin Villeneuve & Sampson LLP

(57) ABSTRACT

Systems and methods may include obtaining data identifying a plurality of cancelled health-related appointments for a plurality of patient records stored in a database, the cancelled health-related appointments associated with a shared health event; associating each of the plurality of patient records with a risk category from a plurality of risk categories ranging from a lowest risk to a highest risk; communicating with a client computing device associated with a patient having a cancelled health-related appointment to schedule a return appointment based at least on a risk category, the communicating including receiving current health condition information of the patient; based on the current health condition information of the patient showing symptoms consistent with symptoms associated with the shared health event, identifying the patient as a potential infected patient; and performing contact tracing based at least on people that the patient has contact with while experiencing the symptoms.

21 Claims, 18 Drawing Sheets

(51) Int. Cl.
*G06V 40/12* (2022.01)
*G06V 40/16* (2022.01)
*G16H 10/60* (2018.01)
*G16H 20/00* (2018.01)
*G16H 40/40* (2018.01)
*G16H 40/63* (2018.01)
*G16H 40/67* (2018.01)
*G16H 50/30* (2018.01)
*G16H 50/70* (2018.01)
*G16H 50/80* (2018.01)
*G16H 80/00* (2018.01)
*G16H 40/20* (2018.01)

(52) U.S. Cl.
CPC ........... *G06V 40/172* (2022.01); *G16H 10/60* (2018.01); *G16H 20/00* (2018.01); *G16H 40/40* (2018.01); *G16H 40/63* (2018.01); *G16H 40/67* (2018.01); *G16H 50/30* (2018.01); *G16H 50/70* (2018.01); *G16H 50/80* (2018.01); *G16H 80/00* (2018.01); *G16H 40/20* (2018.01)

(58) Field of Classification Search
CPC ........ G16H 50/30; G16H 50/70; G16H 50/80; G16H 20/00; G16H 40/40; G16H 40/63; G16H 80/00; G16H 40/20; G06F 21/32
See application file for complete search history.

(56) References Cited

U.S. PATENT DOCUMENTS

| | | |
|---|---|---|
| 5,649,104 A | 7/1997 | Carleton et al. |
| 5,715,450 A | 2/1998 | Ambrose et al. |
| 5,761,419 A | 6/1998 | Schwartz et al. |
| 5,819,038 A | 10/1998 | Carleton et al. |
| 5,821,937 A | 10/1998 | Tonelli et al. |
| 5,831,610 A | 11/1998 | Tonelli et al. |
| 5,873,096 A | 2/1999 | Lim et al. |
| 5,918,159 A | 6/1999 | Fomukong et al. |
| 5,963,953 A | 10/1999 | Cram et al. |
| 5,983,227 A | 11/1999 | Nazem et al. |
| 6,092,083 A | 7/2000 | Brodersen et al. |
| 6,161,149 A | 12/2000 | Achacoso et al. |
| 6,169,534 B1 | 1/2001 | Raffel et al. |
| 6,178,425 B1 | 1/2001 | Brodersen et al. |
| 6,189,011 B1 | 2/2001 | Lim et al. |
| 6,216,133 B1 | 4/2001 | Masthoff |
| 6,216,135 B1 | 4/2001 | Brodersen et al. |
| 6,233,617 B1 | 5/2001 | Rothwein et al. |
| 6,236,978 B1 | 5/2001 | Tuzhilin |
| 6,266,669 B1 | 7/2001 | Brodersen et al. |
| 6,288,717 B1 | 9/2001 | Dunkle |
| 6,295,530 B1 | 9/2001 | Ritchie et al. |
| 6,324,568 B1 | 11/2001 | Diec et al. |
| 6,324,693 B1 | 11/2001 | Brodersen et al. |
| 6,336,137 B1 | 1/2002 | Lee et al. |
| D454,139 S | 3/2002 | Feldcamp et al. |
| 6,367,077 B1 | 4/2002 | Brodersen et al. |
| 6,393,605 B1 | 5/2002 | Loomans |
| 6,405,220 B1 | 6/2002 | Brodersen et al. |
| 6,411,949 B1 | 6/2002 | Schaffer |
| 6,434,550 B1 | 8/2002 | Warner et al. |
| 6,446,089 B1 | 9/2002 | Brodersen et al. |
| 6,535,909 B1 | 3/2003 | Rust |
| 6,549,908 B1 | 4/2003 | Loomans |
| 6,553,563 B2 | 4/2003 | Ambrose et al. |
| 6,560,461 B1 | 5/2003 | Fomukong et al. |
| 6,574,635 B2 | 6/2003 | Stauber et al. |
| 6,577,726 B1 | 6/2003 | Huang et al. |
| 6,601,087 B1 | 7/2003 | Zhu et al. |
| 6,604,117 B2 | 8/2003 | Lim et al. |
| 6,604,128 B2 | 8/2003 | Diec et al. |
| 6,609,150 B2 | 8/2003 | Lee et al. |
| 6,621,834 B1 | 9/2003 | Scherpbier et al. |
| 6,654,032 B1 | 11/2003 | Zhu et al. |
| 6,665,648 B2 | 12/2003 | Brodersen et al. |
| 6,665,655 B1 | 12/2003 | Warner et al. |
| 6,684,438 B2 | 2/2004 | Brodersen et al. |
| 6,711,565 B1 | 3/2004 | Subramaniam et al. |
| 6,724,399 B1 | 4/2004 | Katchour et al. |
| 6,728,702 B1 | 4/2004 | Subramaniam et al. |
| 6,728,960 B1 | 4/2004 | Loomans et al. |
| 6,732,095 B1 | 5/2004 | Warshavsky et al. |
| 6,732,100 B1 | 5/2004 | Brodersen et al. |
| 6,732,111 B2 | 5/2004 | Brodersen et al. |
| 6,754,681 B2 | 6/2004 | Brodersen et al. |
| 6,763,351 B1 | 7/2004 | Subramaniam et al. |
| 6,763,501 B1 | 7/2004 | Zhu et al. |
| 6,768,904 B2 | 7/2004 | Kim |
| 6,772,229 B1 | 8/2004 | Achacoso et al. |
| 6,782,383 B2 | 8/2004 | Subramaniam et al. |
| 6,804,330 B1 | 10/2004 | Jones et al. |
| 6,826,565 B2 | 11/2004 | Ritchie et al. |
| 6,826,582 B1 | 11/2004 | Chatterjee et al. |
| 6,826,745 B2 | 11/2004 | Coker |
| 6,829,655 B1 | 12/2004 | Huang et al. |
| 6,842,748 B1 | 1/2005 | Warner et al. |
| 6,850,895 B2 | 2/2005 | Brodersen et al. |
| 6,850,949 B2 | 2/2005 | Warner et al. |
| 6,907,566 B1 | 6/2005 | McElfresh et al. |
| 7,062,502 B1 | 6/2006 | Kesler |
| 7,069,231 B1 | 6/2006 | Cinarkaya et al. |
| 7,069,497 B1 | 6/2006 | Desai |
| 7,100,111 B2 | 8/2006 | McElfresh et al. |
| 7,181,758 B1 | 2/2007 | Chan |
| 7,269,590 B2 | 9/2007 | Hull et al. |
| 7,289,976 B2 | 10/2007 | Kihneman et al. |
| 7,340,411 B2 | 3/2008 | Cook |
| 7,356,482 B2 | 4/2008 | Frankland et al. |
| 7,373,599 B2 | 5/2008 | McElfresh et al. |
| 7,401,094 B1 | 7/2008 | Kesler |
| 7,406,501 B2 | 7/2008 | Szeto et al. |
| 7,412,455 B2 | 8/2008 | Dillon |
| 7,454,509 B2 | 11/2008 | Boulter et al. |
| 7,508,789 B2 | 3/2009 | Chan |
| 7,599,935 B2 | 10/2009 | La Rotonda et al. |
| 7,603,331 B2 | 10/2009 | Tuzhilin et al. |
| 7,603,483 B2 | 10/2009 | Psounis et al. |
| 7,620,655 B2 | 11/2009 | Larsson et al. |
| 7,644,122 B2 | 1/2010 | Weyer et al. |
| 7,668,861 B2 | 2/2010 | Steven |
| 7,698,160 B2 | 4/2010 | Beaven et al. |
| 7,730,478 B2 | 6/2010 | Weissman |
| 7,747,648 B1 | 6/2010 | Kraft et al. |
| 7,779,039 B2 | 8/2010 | Weissman et al. |
| 7,779,475 B2 | 8/2010 | Jakobson et al. |
| 7,827,208 B2 | 11/2010 | Bosworth et al. |
| 7,853,881 B1 | 12/2010 | Aly Assal et al. |
| 7,945,653 B2 | 5/2011 | Zukerberg et al. |
| 8,005,896 B2 | 8/2011 | Cheah |
| 8,014,943 B2 | 9/2011 | Jakobson |
| 8,015,495 B2 | 9/2011 | Achacoso et al. |
| 8,032,297 B2 | 10/2011 | Jakobson |
| 8,073,850 B1 | 12/2011 | Hubbard et al. |
| 8,082,301 B2 | 12/2011 | Ahlgren et al. |
| 8,095,413 B1 | 1/2012 | Beaven |
| 8,095,531 B2 | 1/2012 | Weissman et al. |
| 8,095,594 B2 | 1/2012 | Beaven et al. |
| 8,103,611 B2 | 1/2012 | Tuzhilin et al. |
| 8,150,913 B2 | 4/2012 | Cheah |
| 8,209,308 B2 | 6/2012 | Rueben et al. |
| 8,209,333 B2 | 6/2012 | Hubbard et al. |
| 8,275,836 B2 | 9/2012 | Beaven et al. |
| 8,457,545 B2 | 6/2013 | Chan |
| 8,484,111 B2 | 7/2013 | Frankland et al. |
| 8,490,025 B2 | 7/2013 | Jakobson et al. |
| 8,504,945 B2 | 8/2013 | Jakobson et al. |
| 8,510,045 B2 | 8/2013 | Rueben et al. |
| 8,510,664 B2 | 8/2013 | Rueben et al. |
| 8,566,301 B2 | 10/2013 | Rueben et al. |
| 8,646,103 B2 | 2/2014 | Jakobson et al. |
| 9,536,052 B2 | 1/2017 | Amarasingham et al. |

(56) References Cited

U.S. PATENT DOCUMENTS

| | | |
|---|---|---|
| 9,996,666 B1 | 6/2018 | Wilson et al. |
| 10,102,926 B1 | 10/2018 | Leonardi |
| 10,296,717 B2 | 5/2019 | Isaacs |
| 10,348,637 B1 | 7/2019 | McNair |
| 10,437,961 B2 | 10/2019 | Nusimow et al. |
| 10,811,139 B1* | 10/2020 | Wang ..................... G06N 20/20 |
| 10,942,664 B2* | 3/2021 | Vandewater ........ G06F 9/44521 |
| 11,056,242 B1 | 7/2021 | Jain et al. |
| 11,126,696 B1 | 9/2021 | Srivastava |
| 11,127,506 B1 | 9/2021 | Jain et al. |
| 11,389,672 B2 | 7/2022 | Santana Rodriguez |
| 11,504,011 B1 | 11/2022 | Jain et al. |
| 11,915,834 B2 | 2/2024 | Ahmed et al. |
| 2001/0044791 A1 | 11/2001 | Richter et al. |
| 2002/0072951 A1 | 6/2002 | Lee et al. |
| 2002/0082892 A1 | 6/2002 | Raffel et al. |
| 2002/0103811 A1 | 8/2002 | Fankhauser et al. |
| 2002/0129352 A1 | 9/2002 | Brodersen et al. |
| 2002/0140731 A1 | 10/2002 | Subramaniam et al. |
| 2002/0143997 A1 | 10/2002 | Huang et al. |
| 2002/0162090 A1 | 10/2002 | Parnell et al. |
| 2002/0165742 A1 | 11/2002 | Robbins |
| 2003/0004971 A1 | 1/2003 | Gong |
| 2003/0018705 A1 | 1/2003 | Chen et al. |
| 2003/0018830 A1 | 1/2003 | Chen et al. |
| 2003/0066031 A1 | 4/2003 | Laane et al. |
| 2003/0066032 A1 | 4/2003 | Ramachandran et al. |
| 2003/0069936 A1 | 4/2003 | Warner et al. |
| 2003/0070000 A1 | 4/2003 | Coker et al. |
| 2003/0070004 A1 | 4/2003 | Mukundan et al. |
| 2003/0070005 A1 | 4/2003 | Mukundan et al. |
| 2003/0074418 A1 | 4/2003 | Coker et al. |
| 2003/0120675 A1 | 6/2003 | Stauber et al. |
| 2003/0151633 A1 | 8/2003 | George et al. |
| 2003/0159136 A1 | 8/2003 | Huang et al. |
| 2003/0187921 A1 | 10/2003 | Diec et al. |
| 2003/0189600 A1 | 10/2003 | Gune et al. |
| 2003/0204427 A1 | 10/2003 | Gune et al. |
| 2003/0206192 A1 | 11/2003 | Chen et al. |
| 2003/0225730 A1 | 12/2003 | Warner et al. |
| 2004/0001092 A1 | 1/2004 | Rothwein et al. |
| 2004/0010489 A1 | 1/2004 | Rio et al. |
| 2004/0015981 A1 | 1/2004 | Coker et al. |
| 2004/0027388 A1 | 2/2004 | Berg et al. |
| 2004/0128001 A1 | 7/2004 | Levin et al. |
| 2004/0186860 A1 | 9/2004 | Lee et al. |
| 2004/0193510 A1 | 9/2004 | Catahan et al. |
| 2004/0199489 A1 | 10/2004 | Barnes-Leon et al. |
| 2004/0199536 A1 | 10/2004 | Barnes-Leon et al. |
| 2004/0199543 A1 | 10/2004 | Braud et al. |
| 2004/0243438 A1 | 12/2004 | Mintz |
| 2004/0249854 A1 | 12/2004 | Barnes-Leon et al. |
| 2004/0260534 A1 | 12/2004 | Pak et al. |
| 2004/0260659 A1 | 12/2004 | Chan et al. |
| 2004/0268299 A1 | 12/2004 | Lei et al. |
| 2005/0050555 A1 | 3/2005 | Exley et al. |
| 2005/0059876 A1 | 3/2005 | Krishnan et al. |
| 2005/0091098 A1 | 4/2005 | Brodersen et al. |
| 2005/0256815 A1 | 11/2005 | Reeve et al. |
| 2006/0036619 A1* | 2/2006 | Fuerst .................... G16H 50/80 |
| 2006/0143044 A1 | 6/2006 | Conry et al. |
| 2007/0027729 A1 | 2/2007 | Bruaene et al. |
| 2007/0194109 A1 | 8/2007 | Harrison et al. |
| 2007/0226007 A1 | 9/2007 | Osaki et al. |
| 2007/0250344 A1 | 10/2007 | Stephenson |
| 2007/0255596 A1 | 11/2007 | Duckert et al. |
| 2008/0120138 A1 | 5/2008 | Morita et al. |
| 2008/0249972 A1 | 10/2008 | Dillon |
| 2009/0063415 A1 | 3/2009 | Chatfield et al. |
| 2009/0100342 A1 | 4/2009 | Jakobson |
| 2009/0112939 A1 | 4/2009 | Sanghvi et al. |
| 2009/0177744 A1 | 7/2009 | Marlow et al. |
| 2010/0036679 A1 | 2/2010 | Rosenberger et al. |
| 2010/0161549 A1 | 6/2010 | Plancarte et al. |
| 2010/0198611 A1 | 8/2010 | Ruoff et al. |
| 2010/0217618 A1* | 8/2010 | Piccirillo ............... G16H 40/20 705/2 |
| 2010/0312581 A1 | 12/2010 | Wachtell et al. |
| 2011/0010087 A1 | 1/2011 | Wons et al. |
| 2011/0218958 A1 | 9/2011 | Warshavsky et al. |
| 2011/0231786 A1 | 9/2011 | Kenney et al. |
| 2011/0247051 A1 | 10/2011 | Bulumulla et al. |
| 2012/0042218 A1 | 2/2012 | Cinarkaya et al. |
| 2012/0173285 A1 | 7/2012 | Muthukrishnan |
| 2012/0191469 A1 | 7/2012 | Akradi |
| 2012/0233137 A1 | 9/2012 | Jakobson et al. |
| 2012/0239560 A1 | 9/2012 | Pourfallah et al. |
| 2012/0290407 A1 | 11/2012 | Hubbard et al. |
| 2013/0031232 A1 | 1/2013 | Clymer et al. |
| 2013/0035948 A1 | 2/2013 | Olalekan |
| 2013/0060576 A1 | 3/2013 | Hamm et al. |
| 2013/0179178 A1 | 7/2013 | Vemireddy et al. |
| 2013/0197930 A1 | 8/2013 | Garibaldi et al. |
| 2013/0197942 A1 | 8/2013 | Chiu et al. |
| 2013/0212497 A1 | 8/2013 | Zelenko et al. |
| 2013/0218948 A1 | 8/2013 | Jakobson |
| 2013/0218949 A1 | 8/2013 | Jakobson |
| 2013/0218966 A1 | 8/2013 | Jakobson |
| 2013/0247216 A1 | 9/2013 | Cinarkaya et al. |
| 2013/0318027 A1 | 11/2013 | Almogy et al. |
| 2014/0019468 A1 | 1/2014 | Federoff et al. |
| 2014/0114618 A1 | 4/2014 | Fonte et al. |
| 2014/0164022 A1 | 6/2014 | Reed et al. |
| 2014/0214199 A1 | 7/2014 | Utech et al. |
| 2014/0359537 A1 | 12/2014 | Jakobson et al. |
| 2015/0006289 A1 | 1/2015 | Jakobson et al. |
| 2015/0007050 A1 | 1/2015 | Jakobson et al. |
| 2015/0095162 A1 | 4/2015 | Jakobson et al. |
| 2015/0142596 A1 | 5/2015 | Jakobson et al. |
| 2015/0172563 A1 | 6/2015 | Jakobson et al. |
| 2015/0213202 A1 | 7/2015 | Amarasingham et al. |
| 2015/0213222 A1 | 7/2015 | Amarasingham et al. |
| 2015/0213225 A1 | 7/2015 | Amarasingham et al. |
| 2015/0215389 A1 | 7/2015 | Spencer |
| 2015/0265162 A1 | 9/2015 | Lavi et al. |
| 2015/0268986 A1 | 9/2015 | De Lima Junior |
| 2015/0301839 A1 | 10/2015 | Bansal |
| 2016/0103856 A1 | 4/2016 | Isaacs |
| 2016/0147562 A1 | 5/2016 | Ferrandiz |
| 2016/0323188 A1 | 11/2016 | Guzman et al. |
| 2017/0011192 A1 | 1/2017 | Arshad et al. |
| 2017/0024531 A1* | 1/2017 | Malaviya ............... G16H 50/30 |
| 2017/0124261 A1 | 5/2017 | Mari |
| 2017/0161439 A1 | 6/2017 | Raduchel et al. |
| 2017/0199189 A1 | 7/2017 | Wade |
| 2017/0209102 A1* | 7/2017 | Parthasarathy ....... A61B 5/0059 |
| 2017/0277854 A1 | 9/2017 | Kelly et al. |
| 2017/0344710 A1 | 11/2017 | Hu et al. |
| 2017/0357771 A1 | 12/2017 | Connolly et al. |
| 2018/0004903 A1 | 1/2018 | Takada et al. |
| 2018/0060494 A1 | 3/2018 | Dias et al. |
| 2018/0121857 A1 | 5/2018 | Gutman et al. |
| 2018/0181713 A1 | 6/2018 | Pillarisetty et al. |
| 2018/0197632 A1 | 7/2018 | Kemp |
| 2018/0336054 A1 | 11/2018 | Sura et al. |
| 2018/0366221 A1* | 12/2018 | Crehore ................ G06F 16/211 |
| 2019/0138624 A1 | 5/2019 | Menendez et al. |
| 2019/0206523 A1 | 7/2019 | Marano et al. |
| 2019/0267133 A1 | 8/2019 | Schwarz et al. |
| 2019/0340156 A1 | 11/2019 | Gupta et al. |
| 2019/0355472 A1 | 11/2019 | Kutzko |
| 2020/0097808 A1* | 3/2020 | Thomas ................ G06Q 10/063 |
| 2020/0242566 A1 | 7/2020 | Agarwal et al. |
| 2020/0251226 A1 | 8/2020 | Vo et al. |
| 2020/0294640 A1 | 9/2020 | Ginsburg |
| 2020/0294680 A1 | 9/2020 | Gupta et al. |
| 2020/0303060 A1 | 9/2020 | Haemel et al. |
| 2020/0411170 A1 | 12/2020 | Brown et al. |
| 2021/0036862 A1 | 2/2021 | Kannan et al. |
| 2021/0142903 A1 | 5/2021 | Mason et al. |
| 2021/0193302 A1 | 6/2021 | Day et al. |
| 2021/0202112 A1 | 7/2021 | Bhatia et al. |
| 2021/0280287 A1 | 9/2021 | Mahmood et al. |
| 2021/0318935 A1 | 10/2021 | Jacobs et al. |

(56) References Cited

U.S. PATENT DOCUMENTS

| | | |
|---|---|---|
| 2021/0319860 A1 | 10/2021 | Ahmed et al. |
| 2021/0319866 A1 | 10/2021 | Ahmed et al. |
| 2021/0319882 A1 | 10/2021 | Ahmed et al. |
| 2021/0319883 A1 | 10/2021 | Ahmed et al. |
| 2021/0319888 A1 | 10/2021 | Ahmed et al. |
| 2021/0319889 A1 | 10/2021 | Ahmed et al. |
| 2021/0319890 A1 | 10/2021 | Ahmed et al. |
| 2021/0319891 A1 | 10/2021 | Ahmed et al. |
| 2021/0319902 A1 | 10/2021 | Ahmed et al. |
| 2021/0319915 A1 | 10/2021 | Ahmed et al. |
| 2021/0319916 A1 | 10/2021 | Ahmed et al. |
| 2021/0319917 A1 | 10/2021 | Ahmed et al. |
| 2021/0383924 A1 | 12/2021 | Rajan et al. |
| 2022/0020456 A1 | 1/2022 | Ahmed et al. |
| 2022/0020460 A1 | 1/2022 | Ahmed et al. |
| 2022/0059230 A1 | 2/2022 | Muse et al. |
| 2022/0101966 A1 | 3/2022 | Goldstein et al. |
| 2022/0157474 A1 | 5/2022 | Gurpur et al. |

OTHER PUBLICATIONS

Hwang, Andrew. Appointment "no shows" are an independent predictor of subsequent quality of care and resource utilization outcomes. J Gen Inter MEd 30(10):1426-33. Mar. 17, 2015. (Year: 2015).*

Kiwanuka, Noah. A randomized trial to assess retention rates using mobile phone reminders versus physical contact tracing in a potential HIV vaccine efficacy population of fishing communities around Lake Victoria, Uganda. BMC Infectious Diseases. 2018. (Year: 2018).*

12. Maxwell. Deep learning architectures for multi-label classification of intelligent health risk prediction. BMC Bioinformatics 2017, 18(Suppl 14):523. (Year: 2017).*

Feng, Zheng. Intelligent Perioperatice System: Towards Real-Time Big Data Analytics in Surgery Risk Assessment. 2017 IEEE 15th Conf on Dependable, Autonomic and Secure Cmputing 15th Intl Conf on Pervasice Intelligence and Computing, 3rd Intl Conf on Big Data Intelligence and Computing and Cyber Scien. (Year: 2017).*

Maxwell. Deep learning architectures for multi-label classification of intelligent health risk prediction. BMC Bioinformatics 2017, 18(Suppl 14):523. (Year: 2017).*

Pagan, Josue. Power transmission and workload balancing policies in eHealth mobile cloud computing scenarios. Future Generation Computer Systems 78 (2018) 587-601. (Year: 2018).*

"Google Plus Users", Google+Ripples, Oct. 31, 2011 [retrieved on Feb. 21, 2012 from Internet at http://www.googleplusers.com/google-ripples.html], 3 pages.

U.S. Appl. No. 16/946,660, filed Jun. 30, 2020, Ahmed et al.

U.S. Appl. No. 16/946,903, filed Jul. 10, 2020, Ahmed et al.

American Collage of Surgeons (ACS) "COVID 19: Elective Case Triage Guidelines for Surgical Care", 2020, pp. 1-38. https://www.facs.org/media/wfjhqOjw/guidance_for_triage_of_nonemergent_surgical_procedures.pdf.

American College of Surgeons (ACS)(Covid-19:Guidance for Triage of Non-Emergent Surgical Procedures.

Arisi I., "Age and Gender Distribution of Covid-19 Infected Cases in Italian Population," Research Square, 2020, pp. 1-16. https://assets.researchsquare.com/files/rs-72021/v1/e3e592bc-2d96-458a-98db-a0ae6712ff47.pdfc=1631854633.

Christian, M.D. et al "Triage- Care of the Critically Ill and Injured During Pandemics and Disasters: CHEST Consensus Statement", CHEST, 2014, vol. 145, No. 4, pp. e61s-e74s. https://journal.chestnet.org/article/S0012-3692(15)51990-9/fulltext.

Craig J M et al., "After the Surge: Prioritizing the Backlog of Delayed Hospital Procedures," BioEthics Forum Essay, https://www.thehastingscenter.org/after-the-surge-prioritizing-the-backlog-of-delayed-hospital-procedures/ (Year: 2020).

Garg S., et al., "Hospitalization Rates and Characteristics of Patients Hospitalized with Laboratory-Confirmed Coronavirus Disease 2019," Morbidity and Mortality Weekly Report, 2020, vol. 69(15), pp. 458-464.https://www.ncbi.nlm.nih.gov/pmc/articles/PMC7755063/ (Year: 2019).

Kopel J., et al., "Racial and Gender-Based Differences in COVID-19," Frontiers Public Health, 2020, vol. 8,—https://www.frontiersin.org/articles/10.3389/fpubh.2020.00418/full.

Kowalczyl, L., "Hospitals Cancel Hundreds of Non-Urgent Procedures, Surgeries, and Medical Appointments" The Boston Globe, Mar. 17, 2020, pp. 6.

Lantry, L., et al., "What's Your State's Coronavirus Reopening Plan?—"Lantry"," Coronavirus Government Response, 2020, pp. 1-27. https://abcnews.go.com/Business/states-coronavirus-reopening-plan/story?id=70565409.

Maroko A., et al., "COVID-19 and Inequity: a Comparative Spatial Analysis of New York City and Chicago Hot Spots," Journal Urban Health, 2020, vol. 97(4), pp. 461-470. https://link.springer.com/article/.

Scott Gottlieb et al., "National coronavirus response: a road map to reopening", The American Enterprise Institute (AEI), Mar. 28, 2020, https://www.aei.org/research-products/report/national-coronavirus-response-a-road-map-to-reopening/ (Year: 2020).

Stahel, P. F. "How to risk-stratify elective surgery during the COVID-19 pandemic?," Patient Saf Surg 14, 8 (2020), https://doi.org/10.1186/s13037-020-00235-9 (Year: 2020).

Tzeng et al., "Cancer Surgery Scheduling During and After the COVID-19 First Wave", Annals of Surgery, Published online May 1, 20208, https://www.ncbi.nlm.nih.gov/pmc/articles/PMC7373457/ (Year: 2020).

U.S. Final office Action dated Sep. 21, 2022 in U.S. Appl. No. 16/949,802.

U.S. Non-Final office Action dated Sep. 21, 2022 in U.S. Appl. No. 16/946,660.

U.S. Final office Action dated Apr. 25, 2022 in U.S. Appl. No. 16/946,660.

U.S. Final Office Action dated Aug. 14, 2023, in U.S. Appl. No. 17/247,037.

U.S. Final Office Action dated Aug. 14, 2023, in U.S. Appl. No. 17/247,865.

U.S. Final Office Action dated Aug. 24, 2023 in U.S. Appl. No. 16/947,763.

U.S. Final Office Action dated Aug. 25, 2023, in U.S. Appl. No. 17/247,307.

U.S. Final Office Action dated Aug. 30, 2023, in U.S. Appl. No. 17/247,427.

U.S. Final office Action dated Jan. 26, 2023 in U.S. Appl. No. 16/946,660.

U.S. Final office Action dated Jan. 26, 2023 in U.S. Appl. No. 16/946,903.

U.S. Final office Action dated Jul. 17, 2023 in U.S. Appl. No. 17/247,114.

U.S. Final Office Action dated Jun. 29, 2023, in U.S. Appl. No. 16/949,802.

U.S. Non Final Office Action dated Mar. 9, 2022, in U.S. Appl. No. 16/949,802.

U.S. Non-Final office Action dated Sep. 12, 2022 in U.S. Appl. No. 16/946,903.

U.S. Non-Final Office Action dated Apr. 4, 2023 in U.S. Appl. No. 16/947,763.

U.S. Non-Final Office Action dated Apr. 6, 2023 in U.S. Appl. No. 17/247,307.

U.S. Non-Final Office Action dated Apr. 14, 2023 in U.S. Appl. No. 17/247,037

U.S. Non-Final office Action dated Apr. 17, 2023 in U.S. Appl. No. 17/247,865

U.S. Non-Final Office Action dated Aug. 1, 2023, in U.S. Appl. No. 17/247,928

U.S. Non-Final Office Action dated Feb. 1, 2023, in U.S. Appl. No. 16/949,802

U.S. Non-Final Office Action dated Feb. 21, 2023, in U.S. Appl. No. 17/247,114

U.S. Non-Final Office Action dated Jul. 13, 2023, in U.S. Appl. No. 17/247,888.

(56) References Cited

OTHER PUBLICATIONS

U.S. Non-Final Office Action dated Mar. 31, 2023 in U.S. Appl. No. 17/247,427.
U.S. Non-Final Office Action dated Sep. 21, 2023, in U.S. Appl. No. 17/248,348.
U.S. Notice of Allowance dated Nov. 13, 2023 in U.S. Appl. No. 17/247,888.
U.S. Office Action dated Dec. 14, 2021 issued in U.S. Appl. No. 16/946,660.
U.S. Office Action dated Dec. 21, 2021 issued in U.S. Appl. No. 16/946,903.
U.S. office action dated Apr. 7, 2022, in U.S. Appl. No. 16/946,903.
Vagal A et al., "Recover Wisely From CO VI D 19: Responsible Resumption of Monurgent Radiology Services," Academic Radiology, vol. 27(10), 13 Pages. https://www.ncbi.nlm.nih.gov/pmc/articles/PMC7 416732/ (Year: 2020).
Wang H., et al., "Using a Partial Differential Equation with Google Mobility Data to Predict COVID-19 in Arizona," Quantitative Biology, 2020, https://arxiv.org/abs/2006.16928.
Wright F T et al., "Breast Cancer Surgery after the Co Vi D-19 Pandemic," Future Medicine, 2020, vol. 16(33), 6 Pages. https :l/www. futuremedicine .com/doi/1 0.2217 /fon-2020-0619 (Year: 2020).
U.S. Final Office Action dated Apr. 4, 2024 in U.S. Appl. No. 17/248,348.
U.S. Final Office Action dated Jul. 1, 2024 in U.S. Appl. No. 17/247,307.
U.S. Final Office Action dated Jun. 17, 2024 in U.S. Appl. No. 17/247,037.
U.S. Final Office Action dated Jun. 28, 2024 in U.S. Appl. No. 16/947,763.
U.S. Final Office Action dated May 30, 2024 in U.S. Appl. No. 17/247,114.
U.S. Non-Final Office Action dated May 7, 2024 in U.S. Appl. No. 17/247,427.
Benavides J., et al., "Transmission of Infectious Diseases en Route to Habitat Hotspots," PLoS ONE, 2012, vol. 7(2) e31290, pp. 1-9, Retrieved from [https://www.ncbi.nlm.nih.gov/pmc/articles/PMC3282722/].
Cosgun O., et al., "Smart Resource Allocation Advisor in the Cloud for COVID-19 and Other Pandemics," IEEE Cloud Summit, 2020, pp. 124-130.
U.S. Final Office Action dated Jan. 30, 2024 in U.S. Appl. No. 17/247,928.
U.S. Non-Final Office Action dated Dec. 6, 2023 in U.S. Appl. No. 17/247,114.
U.S. Non-Final Office Action dated Feb. 21, 2024 in U.S. Appl. No. 17/247,037.
U.S. Non-Final Office Action dated Feb. 22, 2024 in U.S. Appl. No. 17/247,307.
U.S. Non-Final Office Action dated Feb. 22, 2024 in U.S. Appl. No. 17/247,865.
U.S. Non-Final Office Action dated Jan. 26, 2024 in U.S. Appl. No. 16/947,763.
U.S. Final Office Action dated Jul. 11, 2024 in U.S. Appl. No. 17/247,865.
U.S. Non-Final Office Action dated Aug. 14, 2024 in U.S. Appl. No. 17/248,348.
U.S. Non-Final Office Action dated Jul. 16, 2024 in U.S. Appl. No. 17/247,928.

\* cited by examiner

| ReOpening Phase / Patient Risk Category | First Phase (highest risk) | Second Phase | Third Phase | Fourth Phase (lowest risk) |
|---|---|---|---|---|
| Category 1 (highest risk) | 1 | 1 | 1 | 2 |
| Category 2 | 1 | 1 | 2 | 2 |
| Category 3 | 1 | 2 | 2 | 3 |
| Category 4 (lowest risk) | 1 | 3 | 3 | 4 |

PROACTIVE CONTACT TRACING ASSOCIATED WITH SHARED HEALTH EVENTS

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

TECHNICAL FIELD

The present disclosure relates generally to data processing and more specifically relates to performing contact tracing related to a shared health event.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art.

The current situation with Covid-19 has caused many medical appointments including elective surgeries to be cancelled. This presents a major issue of how the medical care facilities will handle re-scheduling a huge backlog of patients waiting to be treated. The longer the situation with Covid-19 continues, the larger the backlog will become. One solution to control the spread of Covid-19 is contact tracing. However, since the current approach to contact tracing relies on self-reporting, the solution is not efficient because not everyone self-reports in a timely manner, and some may not self-report at all.

BRIEF DESCRIPTION OF THE DRAWINGS

The included drawings are for illustrative purposes and serve only to provide examples of possible structures and process operations for the disclosed techniques. These drawings in no way limit any changes in form and detail that may be made to implementations by one skilled in the art without departing from the spirit and scope of the disclosure.

FIG. 5C shows an example score table generated using the risk categories for a patient and the risk level associated with reopening phases, in accordance with some implementations.

DETAILED DESCRIPTION

Figure 1:
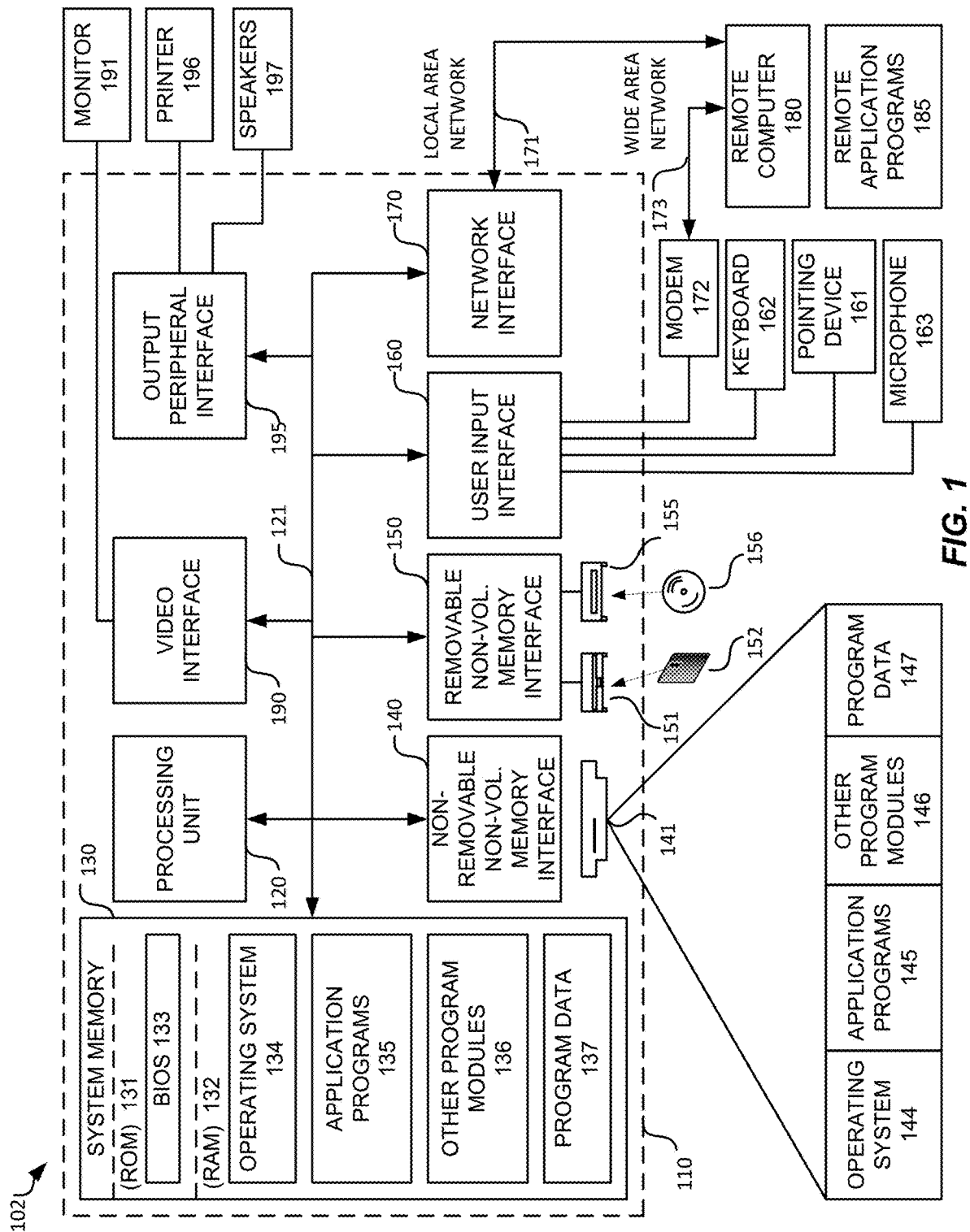
FIG. 1 shows a diagram of an example computing system that may be used with some implementations.

The situation with Covid-19 has caused many people to become ill. According to the United States Central for Disease Control (CDC), as updated on Jun. 25, 2020, COVID-19 can affect anyone, and the disease can cause symptoms ranging from mild to very severe. Some people are more likely to develop severe COVID-19 illness. These are generally referred to as risk factors. People with the risk factors may be more likely to have severe illness if they have COVID-19, and they may be better cared for in a controlled environment such as, for example, a hospital where healthcare resources are more readily available.

Some implementations may include systems and methods for performing contact tracing for a plurality of patients whose health-related appointments are cancelled because of a shared health event. An example of a shared health event is Covid-19 or a pandemic. Since these patients are associated with cancelled health-related appointments, it may be likely that they have certain medical conditions, and they may possibly be taking medications. As such, the patients associated with cancelled health-related appointments may be considered to have the risk factors identified by a governmental health department or a health organization.

Examples of systems and methods associated with performing contact tracing for a plurality of patients whose health-related appointments are cancelled when there is a shared health event will be described with reference to some implementations. Contact tracing is used by the health departments to prevent the spread of infectious disease such as Covid-19. In general, contact tracing involves identifying people who have an infectious disease and people who they came in contact with. The goal of contact tracing is to stop or interrupt the spread of the disease. For example, this may include asking the infected people to isolate and their contacts to do a self-quarantine.

The examples are being provided solely to add context and aid in the understanding of the present disclosure. It will thus be apparent to one skilled in the art that the techniques described herein may be practiced without some or all of these specific details. In other instances, well known process operations have not been described in detail in order to avoid unnecessarily obscuring the present disclosure. Other applications are possible, such that the following examples should not be taken as definitive or limiting either in scope or setting.

In the following detailed description, references are made to the accompanying drawings, which form a part of the description and in which are shown, by way of illustration, some implementations. Although these implementations are described in sufficient detail to enable one skilled in the art to practice the disclosure, it is understood that these examples are not limiting, such that other implementations may be used and changes may be made without departing from the spirit and scope of the disclosure.

As used herein, the term "multi-tenant database system" refers to those systems in which various elements of hardware and software of the database system may be shared by one or more customers. For example, a given application server may simultaneously process requests for a great number of customers, and a given database table may store rows for a potentially much greater number of customers.

The described subject matter may be implemented in the context of any computer-implemented system, such as a software-based system, a database system, a multi-tenant environment, or the like. Moreover, the described subject matter may be implemented in connection with two or more separate and distinct computer-implemented systems that cooperate and communicate with one another. One or more examples may be implemented in numerous ways, including as a process, an apparatus, a system, a device, a method, a computer readable medium such as a computer readable storage medium containing computer readable instructions or computer program code, or as a computer program product comprising a computer usable medium having a computer readable program code embodied therein.

The disclosed implementations may include a computer-implemented method to perform contact tracing for a plurality of patients related to a shared health event and may include obtaining, from a database, data identifying a plurality of cancelled health-related appointments for a plurality of patient records stored in the database, the cancelled health-related appointments associated with a shared health event; associating, by a server computing system, each of the plurality of patient records with a risk category from a plurality of risk categories ranging from a lowest risk to a highest risk, wherein a risk category is determined based on a health-related need associated with a cancelled health-related appointment; communicating, by the server computing system, with a client device associated with a patient to schedule a return appointment based at least on the risk category associated with the patient record associated with the patient, the communicating including receiving, by the server computing system, current health condition information of the patient; based on the current health condition information showing symptoms consistent with symptoms of the shared health event, identifying, by the server computing system, the patient as a potential infected patient and performing, by the server computing system, contact tracing based at least on people that the patient has contact with.

The disclosed implementations may include a system for performing contact tracing, the system comprising a database system implemented using a server computing system, the database system configurable to cause obtaining, from a database, data identifying a plurality of cancelled health-related appointments for a plurality of patient records stored in the database, the cancelled health-related appointments associated with a shared health event; associating, by the server computing system, each of the plurality of patient records with a risk category from a plurality of risk categories ranging from a lowest risk to a highest risk, wherein a risk category is determined based on a treatment associated with a cancelled health-related appointment and a medical history of a patient associated with the cancelled health-related appointment; communicating, by the server computing system, with a client device associated with a patient to schedule a return appointment based at least on the risk category associated with the patient record associated with the patient, the communicating including receiving, by the server computing system, current health condition information of the patient; based on the current health condition information showing symptoms consistent with a cause of the shared health event, identifying, by the server computing system, the patient as a potential infected patient; and performing, by the server computing system, contact tracing based at least on people that the patient has contact with.

The disclosed implementations may include a computer program product comprising computer-readable program code to be executed by one or more processors of a server computing system when retrieved from a non-transitory computer-readable medium, the program code including instructions to obtain, from a database, data identifying a plurality of cancelled health-related appointments for a plurality of patient records stored in the database, the cancelled health-related appointments associated with a shared health event; associate each of the plurality of patient records with a risk category from a plurality of risk categories ranging from a lowest risk to a highest risk, wherein a risk category is determined based on a treatment associated with a cancelled health-related appointment and a medical history of a patient associated with the cancelled health-related appointment; communicate with a client device associated with a patient to schedule a return appointment based at least on the risk category associated with the patient record associated with the patient, the communicating including receiving current health condition information of the patient; based on the current health condition information showing symptoms consistent with a cause of the shared health event, identify the patient as a potential infected patient; and perform contact tracing based at least on people that the patient has contact with.

While one or more implementations and techniques are described with reference to performing contact tracing for a plurality of patients whose health-related appointments are cancelled because of a shared health event implemented in a system having an application server providing a front end for an on-demand database service capable of supporting multiple tenants, the one or more implementations and techniques are not limited to multi-tenant databases nor deployment on application servers. Implementations may be practiced using other database architectures, i.e., ORACLE®, DB2® by IBM and the like without departing from the scope of the claimed subject matter. Further, some implementations may include using Hardware Security Module (HSM), a physical computing device that safeguards and manages digital keys for strong authentication, including, for example, the keys used to encrypt secrets associated with the data elements stored in the data stores. It may be noted that the term "data store" may refer to source control systems, file storage, virtual file systems, non-relational databases (such as NoSQL), etc.

Any of the above implementations may be used alone or together with one another in any combination. The one or more implementations encompassed within this specification may also include examples that are only partially mentioned or alluded to or are not mentioned or alluded to at all in this brief summary or in the abstract. Although various implementations may have been motivated by various deficiencies with the prior art, which may be discussed or alluded to in one or more places in the specification, the implementations do not necessarily address any of these deficiencies. In other words, different implementations may address different deficiencies that may be discussed in the specification. Some implementations may only partially address some deficiencies or just one deficiency that may be discussed in the specification, and some implementations may not address any of these deficiencies.

FIG. 1 is a diagram of an example computing system that may be used with some implementations. In diagram 102, computing system 110 may be used by a user to establish a connection with a server computing system. The computing system 110 is only one example of a suitable computing system, such as a mobile computing system, and is not intended to suggest any limitation as to the scope of use or functionality of the design. Neither should the computing system 110 be interpreted as having any dependency or requirement relating to any one or combination of components illustrated. The design is operational with numerous other general-purpose or special-purpose computing systems. Examples of well-known computing systems, environments, and/or configurations that may be suitable for use with the design include, but are not limited to, personal computers, server computers, hand-held or laptop devices, multiprocessor systems, microprocessor-based systems, set top boxes, programmable consumer electronics, mini-computers, mainframe computers, distributed computing environments that include any of the above systems or devices, and the like. For example, the computing system 110 may be implemented as a mobile computing system such as one that is configured to run with an operating system (e.g., iOS) developed by Apple Inc. of Cupertino, California or an operating system (e.g., Android) that is developed by Google Inc. of Mountain View, California.

Some implementations may be described in the general context of computing system executable instructions, such as program modules, being executed by a computer. Generally, program modules include routines, programs, objects, components, data structures, etc. that performs particular tasks or implement particular abstract data types. Those skilled in the art can implement the description and/or figures herein as computer-executable instructions, which can be embodied on any form of computing machine program product discussed below.

Some implementations may also be practiced in distributed computing environments where tasks are performed by remote processing devices that are linked through a communications network. In a distributed computing environment, program modules may be located in both local and remote computer storage media including memory storage devices.

Referring to FIG. 1, the computing system 110 may include, but are not limited to, a processing unit 120 having one or more processing cores, a system memory 130, and a system bus 121 that couples with various system components including the system memory 130 to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) locale bus, and Peripheral Component Interconnect (PCI) bus also known as Mezzanine bus.

The computing system 110 typically includes a variety of computer program product. Computer program product can be any available media that can be accessed by computing system 110 and includes both volatile and nonvolatile media, removable and non-removable media. By way of example, and not limitation, computer program product may store information such as computer readable instructions, data structures, program modules or other data. Computer storage media include, but are not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 110. Communication media typically embodies computer readable instructions, data structures, or program modules.

The system memory 130 may include computer storage media in the form of volatile and/or nonvolatile memory such as read only memory (ROM) 131 and random access memory (RAM) 132. A basic input/output system (BIOS) 133, containing the basic routines that help to transfer information between elements within computing system 110, such as during start-up, is typically stored in ROM 131. RAM 132 typically contains data and/or program modules that are immediately accessible to and/or presently being operated on by processing unit 120. By way of example, and not limitation, FIG. 1 also illustrates operating system 134, application programs 135, other program modules 136, and program data 137.

The computing system 110 may also include other removable/non-removable volatile/nonvolatile computer storage media. By way of example only, FIG. 1 also illustrates a hard disk drive 141 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156 such as, for example, a CD ROM or other optical media. Other removable/non-removable, volatile/nonvolatile computer storage media that can be used in the exemplary operating environment include, but are not limited to, USB drives and devices, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 1, provide storage of computer readable instructions, data structures, program modules and other data for the computing system 110. In FIG. 1, for example, hard disk drive 141 is illustrated as storing operating system 144, application programs 145, other program modules 146, and program data 147. Note that these components can either be the same as or different from operating system 134, application programs 135, other program modules 136, and program data 137. The operating system 144, the application programs 145, the other program modules 146, and the program data 147 are given different numeric identification here to illustrate that, at a minimum, they are different copies.

A user may enter commands and information into the computing system 110 through input devices such as a keyboard 162, a microphone 163, and a pointing device 161, such as a mouse, trackball or touch pad or touch screen. Other input devices (not shown) may include a joystick, game pad, scanner, or the like. These and other input devices are often connected to the processing unit 120 through a user input interface 160 that is coupled with the system bus 121, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 190.

The computing system 110 may operate in a networked environment using logical connections to one or more remote computers, such as a remote computer 180. The remote computer 180 may be a personal computer, a handheld device, a server, a router, a network PC, a peer device or other common network node, and typically includes many or all of the elements described above relative to the computing system 110. The logical connections depicted in FIG. 1 include a local area network (LAN) 171 and a wide area network (WAN) 173 but may also include other networks. Such networking environments are commonplace in offices, enterprise-wide computer networks, intranets and the Internet.

FIG. 1 includes a local area network (LAN) 171 and a wide area network (WAN) 173 but may also include other networks. Such networking environments are commonplace in offices, enterprise-wide computer networks, intranets and the Internet.

When used in a LAN networking environment, the computing system 110 may be connected to the LAN 171 through a network interface or adapter 170. When used in a WAN networking environment, the computing system 110 typically includes a modem 172 or other means for establishing communications over the WAN 173, such as the Internet. The modem 172, which may be internal or external, may be connected to the system bus 121 via the user-input interface 160, or other appropriate mechanism. In a networked environment, program modules depicted relative to the computing system 110, or portions thereof, may be stored in a remote memory storage device. By way of example, and not limitation, FIG. 1 illustrates remote application programs 185 as residing on remote computer 180. It will be appreciated that the network connections shown are exemplary and other means of establishing a communications link between the computers may be used.

It should be noted that some implementations may be carried out on a computing system such as that described with respect to FIG. 1. However, some implementations may be carried out on a server, a computer devoted to message handling, handheld devices, or on a distributed system in which different portions of the present design may be carried out on different parts of the distributed computing system.

Another device that may be coupled with the system bus 121 is a power supply such as a battery or a Direct Current (DC) power supply) and Alternating Current (AC) adapter circuit. The DC power supply may be a battery, a fuel cell, or similar DC power source needs to be recharged on a periodic basis. The communication module (or modem) 172 may employ a Wireless Application Protocol (WAP) to establish a wireless communication channel. The communication module 172 may implement a wireless networking standard such as Institute of Electrical and Electronics Engineers (IEEE) 802.11 standard, IEEE std. 802.11-1999, published by IEEE in 1999.

Examples of mobile computing systems may be a laptop computer, a tablet computer, a Netbook, a smart phone, a personal digital assistant, or other similar device with on board processing power and wireless communications ability that is powered by a Direct Current (DC) power source that supplies DC voltage to the mobile computing system and that is solely within the mobile computing system and needs to be recharged on a periodic basis, such as a fuel cell or a battery.

Figure 2:
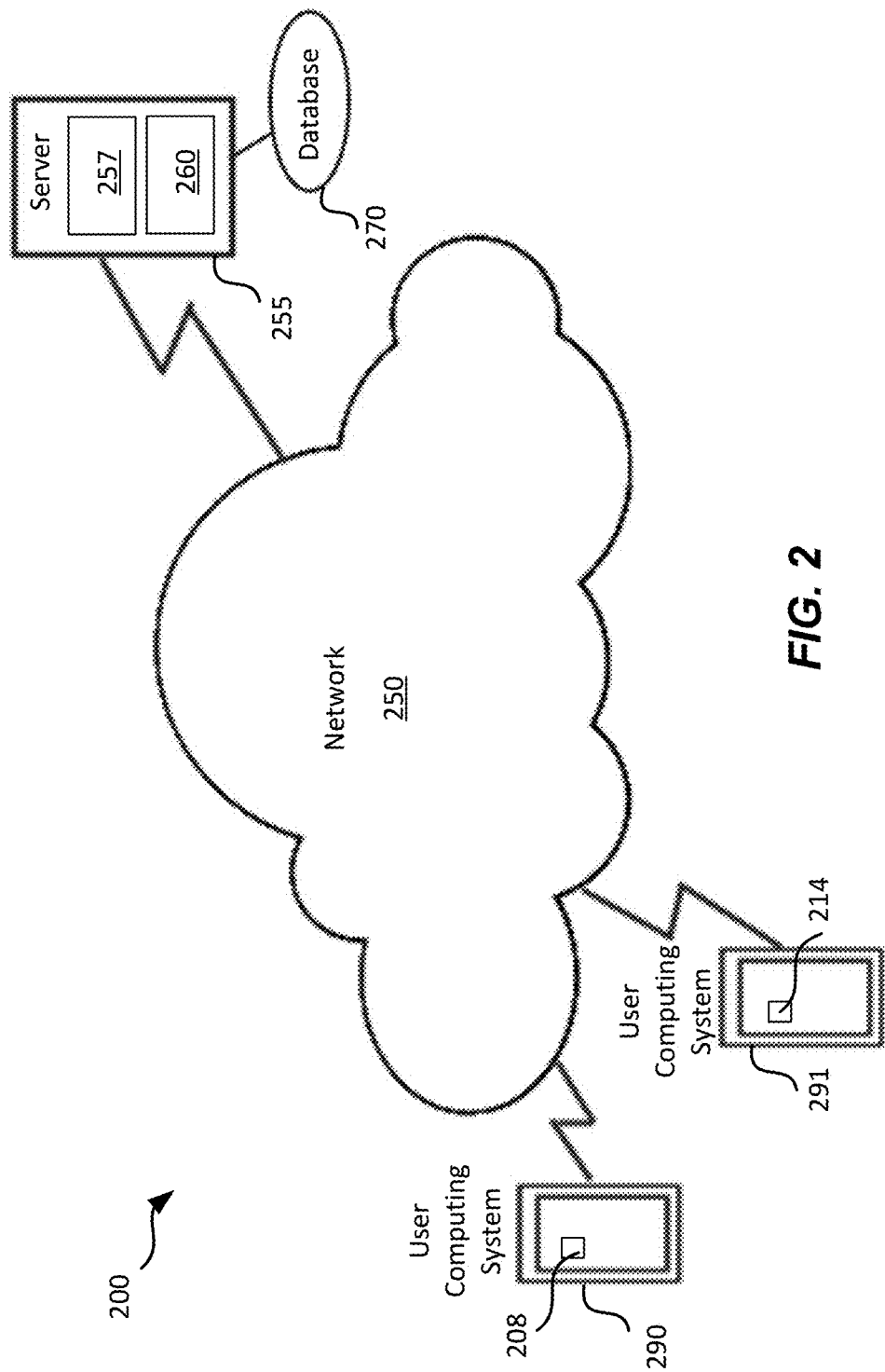
FIG. 2 shows a diagram of an example network environment that may be used with some implementations.

FIG. 2 shows a diagram of an example network environment that may be used with some implementations. Diagram 200 includes computing systems 290 and 291. One or more of the computing systems 290 and 291 may be a mobile computing system. The computing systems 290 and 291 may be connected to the network 250 via a cellular connection or via a Wi-Fi router (not shown). The network 250 may be the Internet. The computing systems 290 and 291 may be coupled with server computing systems 255 via the network 250. The server computing system 255 may be coupled with database 270.

Each of the computing systems 290 and 291 may include an application module such as module 208 or 214. For example, a user may use the computing system 290 and the application module 208 to connect to and communicate with the server computing system 255 and log into application 257 (e.g., a Salesforce.com® application).

For some implementations, one of the computing systems 290 and 291 may be used by an administrator. The administrator may be associated with a healthcare system 305 (shown in FIG. 3A). The administrator may log into the healthcare system 305 via the application 257. The administrator may then launch the application 260 (also referred to as rescheduling module 260). The rescheduling module 260 may be coupled with database 270 which may be configured to store patient health records associated with a plurality of patients. The database 270 may span across multiple database systems and may include multiple databases that may be used by the rescheduling module 260 to schedule each of the plurality of patients for return appointments. For some implementations, the database 270 may be configured to store appointment information of the plurality of patients. For some implementations, the appointment information may include information about cancelled appointments because of a shared-health event.

Figure 3A:
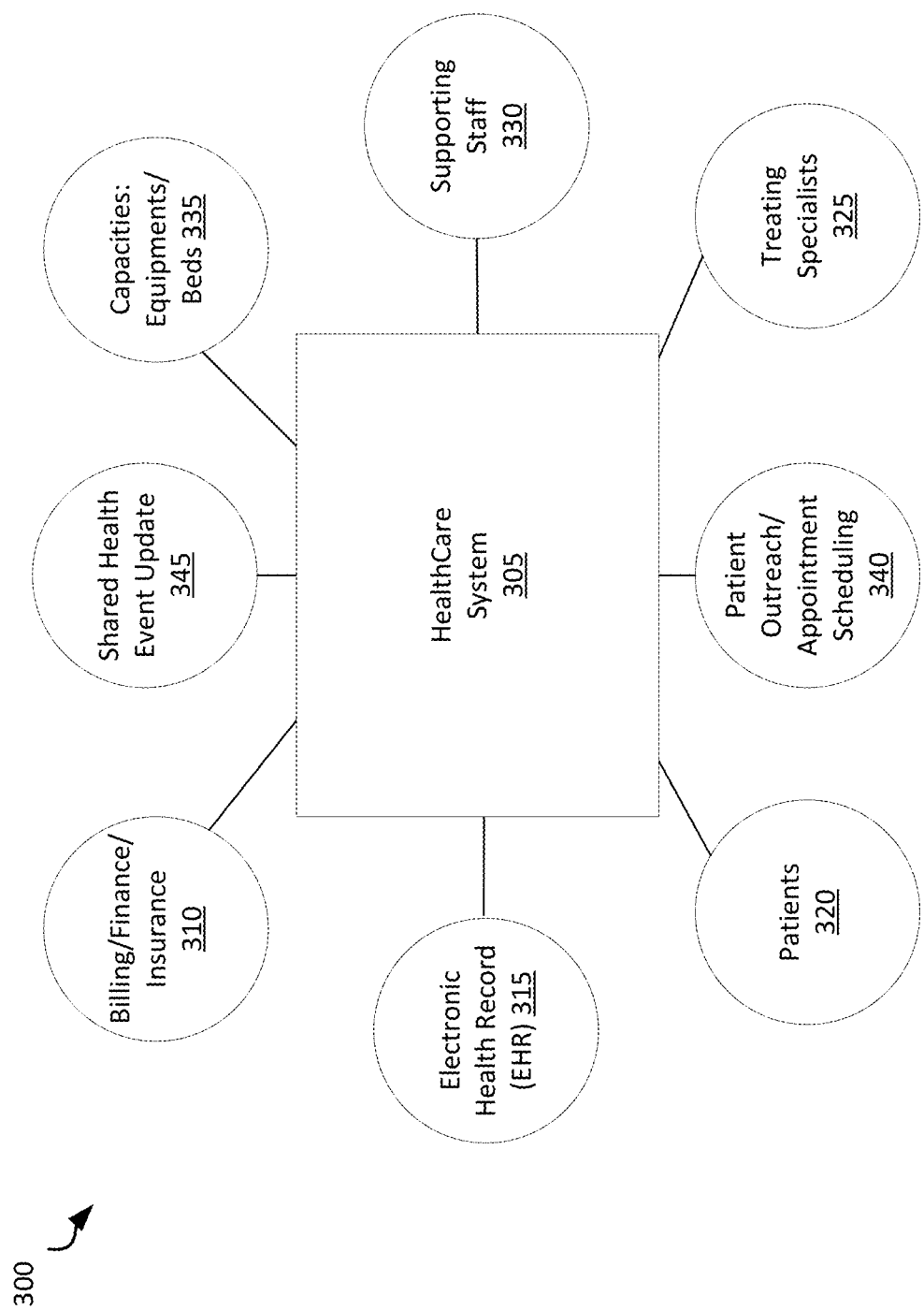
FIG. 3A shows an example healthcare system, in accordance with some implementations.

FIG. 3A shows an example of a healthcare system, in accordance with some implementations. The healthcare system 305 in diagram 300 may be associated with a hospital, a medical group, a system of hospitals or with any health care provider providing health care related services to a plurality of patients. For example, the healthcare system 305 may be implemented as a tenant in a multi-tenant environment and may be associated with a system having an application server providing a front end for an on-demand database service capable of supporting multiple tenants. The healthcare system 305 may be part of one system, or it may span several systems across multiple geographical areas.

For some implementations, the healthcare system 305 may be configured to cause performing operations related to managing available physical resources and physical capacities such as equipments and beds 335. For some implementations, the healthcare system 305 may be configured to cause performing operations related to managing available human resources or human capacities such as treating specialists 325 and supporting staff 330. For some implementations, the healthcare system 305 may be configured to cause performing operations related to patient outreach which may include communicating with the patients 320 to let them know that the hospitals or medical providers are open for business again and will be rebooking or rescheduling them and guide them through a scheduling process for return appointments. This may be performed by the customer outreach and patient appointment scheduling module 340. For some implementations, the healthcare system 305 may be configured to cause operations related to billing, finance or insurance payment 310 to process billing and to determine margin and revenue mix, collect payments for treatments provided to the plurality of patients 320. This may include operations related to completing insurance forms, filling out forms related to the intake processes, etc.

For some implementations, the healthcare system 305 may be configured to cause accessing an electronic health record (EHR) 315 to access patient health records for the plurality of patients 320. The EHR 315 may also be referred to as electronic medical record (EMR). The EHR 315 may be configured to store patient health records of patients associated with the healthcare system 305. For example, a patient health record may include information about a patient's most current health condition as well as information about past health condition. For some implementations, a patient health record may include information about past surgeries, type of treatments received, immunization dates, allergies, radiology images, laboratory and test results, hospital stay, past appointments, and insurance coverage information when applicable. For some implementations, a patient health record may also include characteristic information about a patient including, for example, age, racial background, education background, gender, employment information and current contact information including mailing address, telephone number and email address.

For some implementations, when there is a shared health event such as, for example, a pandemic, the healthcare system 305 may be configured to cause receiving shared health event update 345 from one or more of local, national and international health organization such as, for example, Center for Disease Control (CDC) and World Health Organization (WHO). For example, the shared health event update 345 may include information about the different reopening phases associated with the shared health event.

Figure 3B:
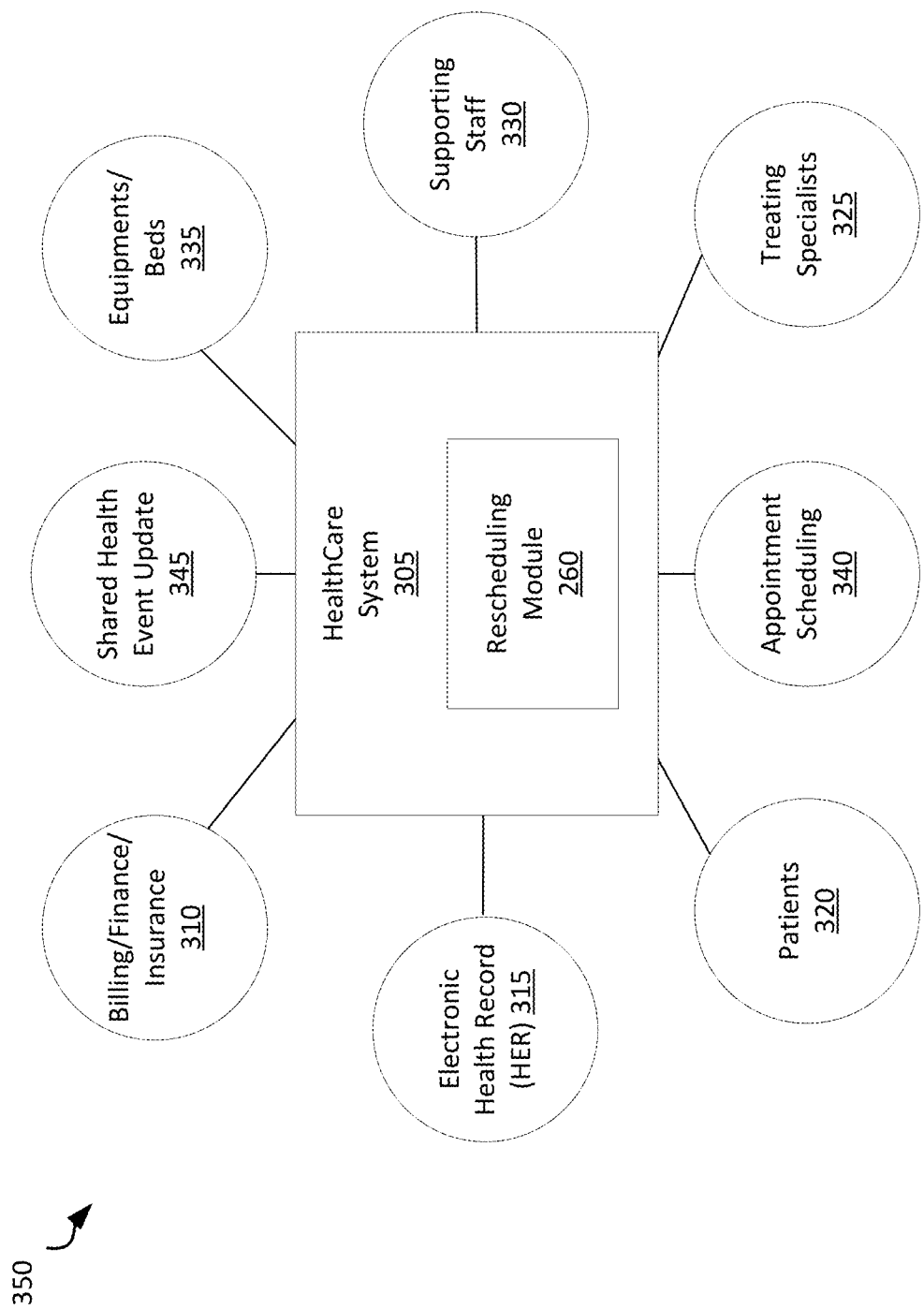
FIG. 3B shows an example healthcare system and its rescheduling module, in accordance with some implementations.

FIG. 3B shows an example healthcare system and its rescheduling module, in accordance with some implementations. The healthcare system 305 in diagram 350 may be configured to cause performing health assessment of a plurality of patients within a certain time frame so that the plurality of patients can receive treatments delayed by a shared health event. For example, at or near the end of the shared health event, the patients whose treatments were delayed may need to be treated as soon as possible if their condition fit certain criteria. The health assessment operations may be performed by the rescheduling module 260. The rescheduling module 260 may be configured to evaluate each patient based on multiple factors such that an order may be established to schedule the plurality of patients to return for the treatments.

Figure 3C:
FIGS. 3C-3D show examples of reopening phases, in accordance with some implementations.
Figure 3D:
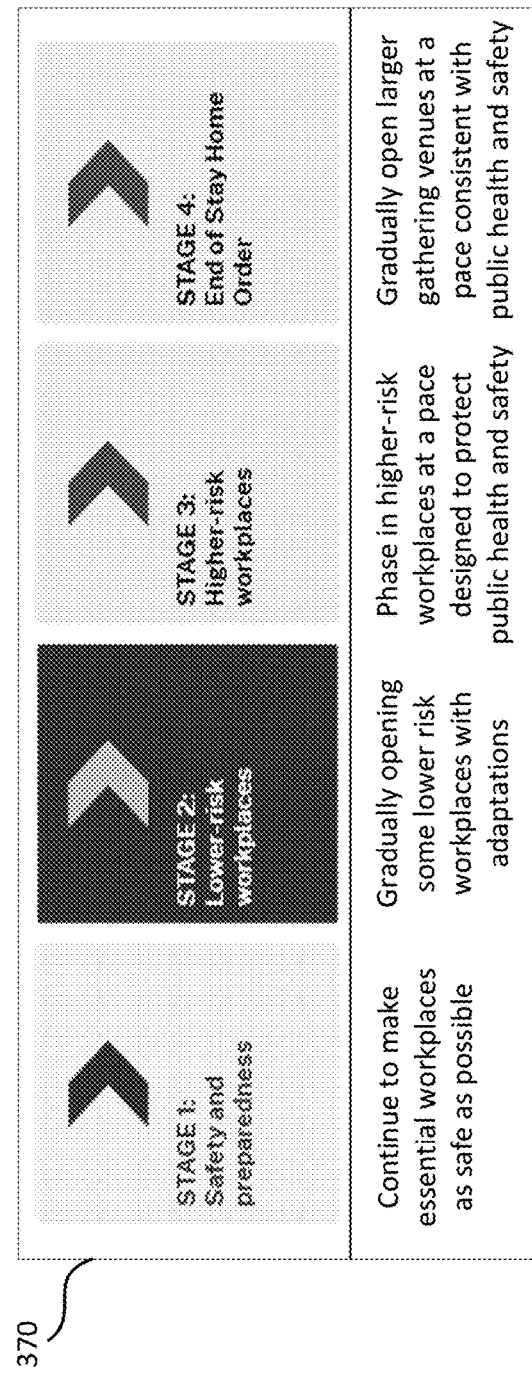

FIGS. 3C-3D show examples of reopening phases, in accordance with some implementations. Reopening phases 360 shown in FIG. 3C may correspond to the reopening phases from Covid-19 as applied in the state of New York. Reopening phases 370 shown in FIG. 3D may correspond to the reopening phases from Covid-19 as applied in the state of California. It may be noticed that the reopening phases 360 and 370 are different from one another, even though they are both applicable to Covid-19. There are three phases in the reopening phases 360, with phase 1 being most dangerous to high risk individuals, and they must stay at home. Phase 2 of the reopening phases 360 may be more open and businesses may resume operations but require practicing of social distancing. Phase 3 of the reopening phases 360 may be least restrictive where businesses may resume normal operations with normal staffing. In comparison, there are four phases in the reopening phases 370 with phase 1 being most restrictive, phases 2 and 3 may be applicable to reopening workplaces at lower risks and those at higher risks respectively, while phase 4 may be applicable to end of stay at home order and gradual opening of larger gathering venues.

It may be noticed that, since the reopening phases may be different for different areas (e.g., New York vs. California), it is possible that the timing of the reopening phases are also different. For example, while the state of New York may start the reopening phase 3 on Aug. 15, 2020, the state of California may start the reopening phase 3 on Jul. 15, 2020. It may also be noticed that the difference in the phases may be based on the difference in population density. For example, an area that has a large population may be associated with the reopening phases that may span over a longer time period as compared to an area of similar size but with a smaller population. The reopening phases may also vary based on availability of vaccine. For example, in an area where the vaccine is very accessible, the reopening phases may be more aggressive than an area where accessing the vaccine is difficult or not easily accessible.

For some implementations, a risk level may be associated with each reopening phase for a geographical area. The risk level may decrease as more safety measures such as, for example, social distancing requirements, mask requirements, etc. are put in place and practiced by members of the geographical area. For example, there may be a higher risk of being exposed to Covid-19 during reopening phase 1 of California than during the reopening phase 3 of California. For some implementations, the risk level associated with the reopening phases of a shared health event (e.g., Covid-19) may be considered in scheduling the plurality of patients for return appointments. For example, less patients may be scheduled for return appointment during reopening phase 1 in California, and more patients may be scheduled for return appointments during reopening phase 3 in California. As another example, patients with serious underlying condition such as heart disease may be less likely to be scheduled for a return appointment during the reopening phase 1 in California, but more likely to be scheduled for a return appointment during the reopening phase 3 in California.

For some implementations, a current reopening phase may be rolled back due to change to the shared health event, and the rescheduling of the patients for the return appointments may reflect the rolled back reopening phase. For example, the change in the shared health event may reflect a situation when the shared health event may become worse when it was expected to be better, and a current reopening phase (e.g., phase 3) may revert back to a previous reopening phase (e.g., phase 2) instead of the next reopening phase (e.g., phase 4).

Figure 3E:
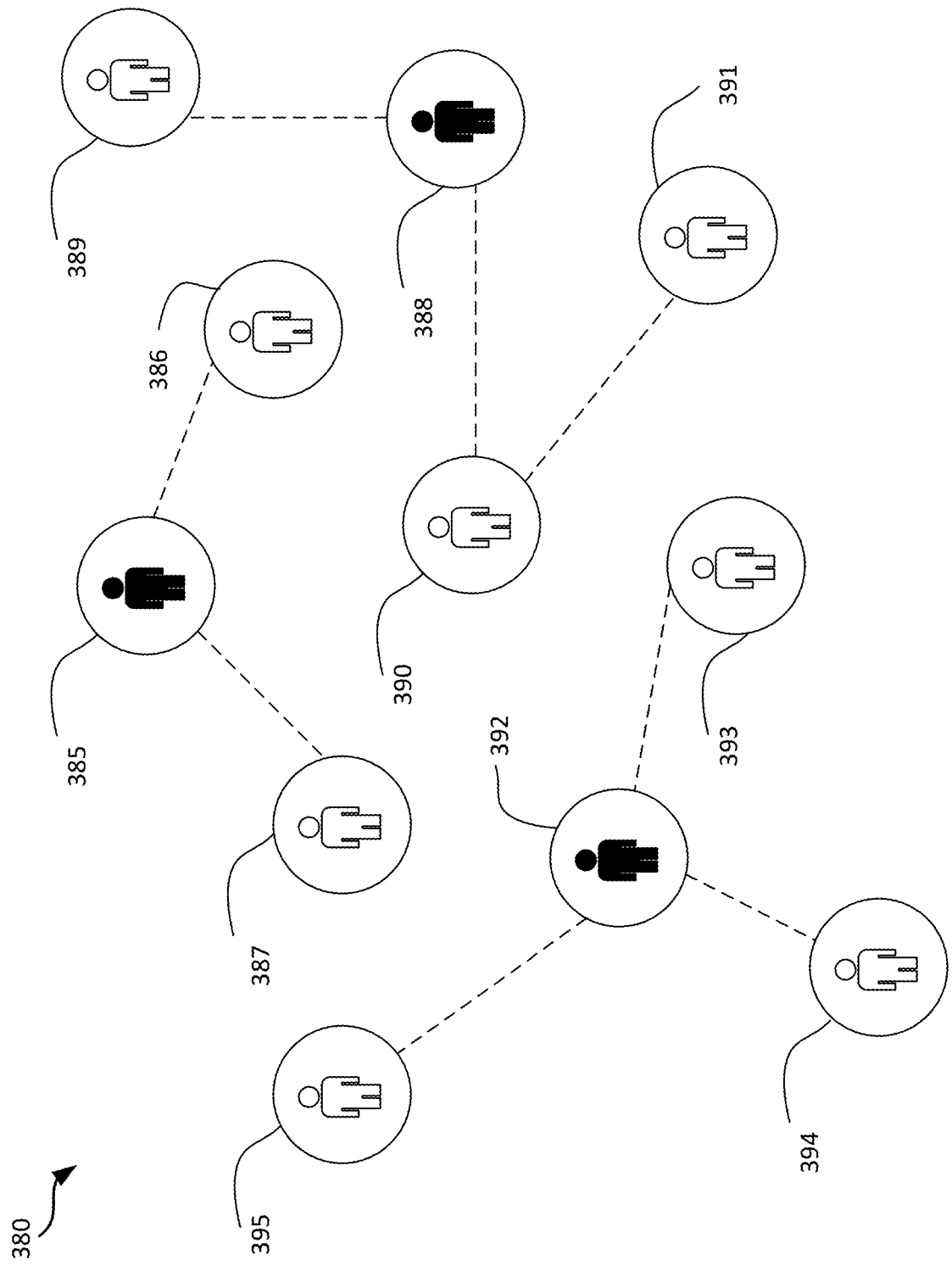
FIG. 3E shows some example patients connected based on contacts, in accordance with some implementations.

FIG. 3E shows some example patients connected based on contacts, in accordance with some implementations. Patients 385, 388 and 392 may be some of the plurality of patients whose health-related appointment are cancelled because of the shared health event. The patient 385 may be in contact with the people 386, 387. The patient 388 may be in contact with the people 389, 390 and 391. The patient 392 may be in contact with the people 393, 394 and 395. It may be possible that one or more of the patients 385, 388 and 392 may be experiencing symptoms that are consistent with the symptoms of a shared health event. In that situation, they may be infected with a disease associated with the shared health event, and they may be spreading the disease to the people that they have contact with. It may be possible that one or more of the patients 385, 388 and 392 don't know they are infected to self-report, or if they know how to self-report, they may not do that in a timely manner. For some implementations, the rescheduling module 260 may be configured to communicate with a device or computing system associated with the patients to identify if the patients have symptoms consistent with the symptoms associated with the shared-health event.

Figure 4A:
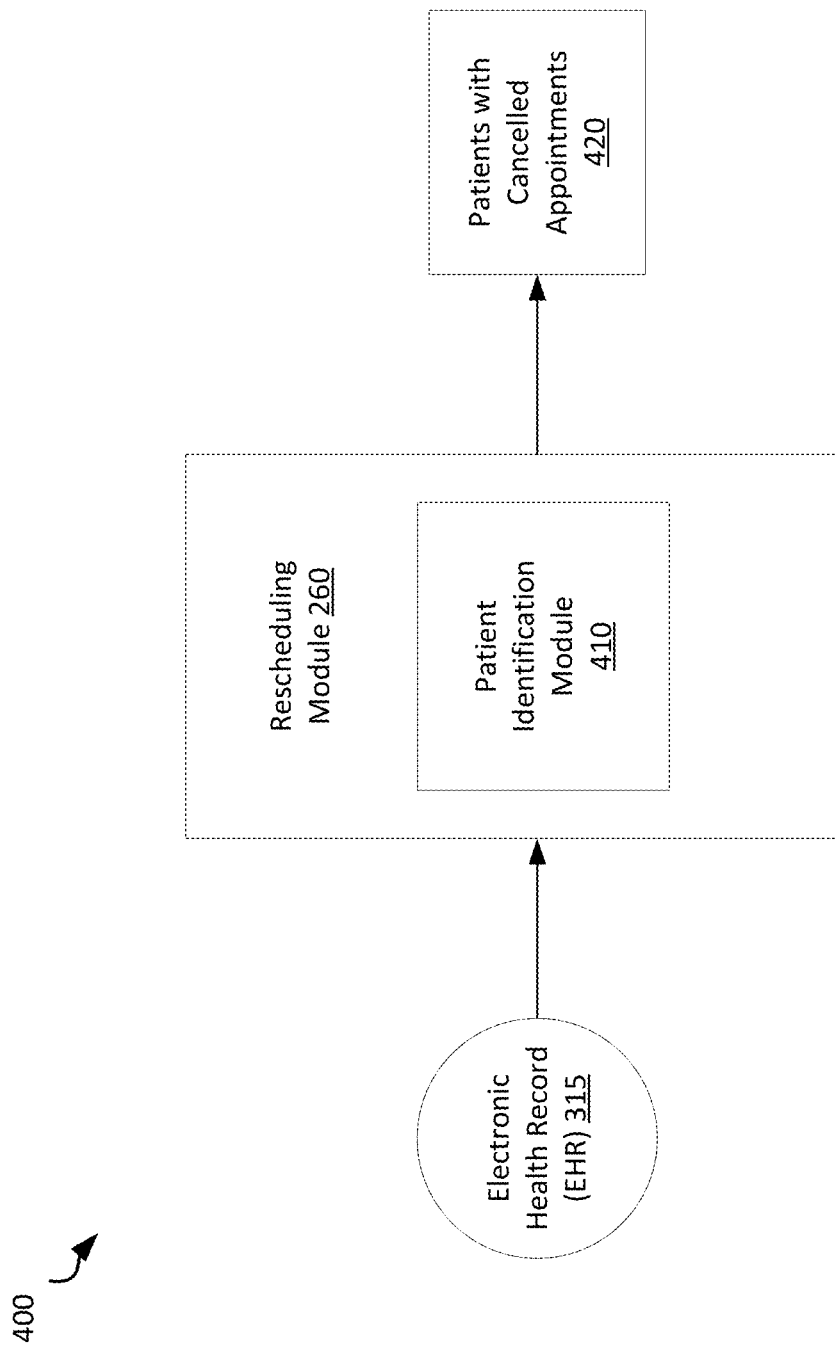
FIG. 4A shows an example rescheduling module with its patient identification operation, in accordance with some implementations.

FIG. 4A shows an example rescheduling module with its patient identification operation, in accordance with some implementations. As shown in diagram 400, the rescheduling module 260 may be configured to include a patient identification module 410. For some implementations, when the treatments or health-related need of the plurality of patients are delayed by the shared health event, their patient records in the EHR 315 may be updated. For some implementations, the patient identification module 410 may be configured to retrieve patient health records from the EHR 315 and identify the patients whose health-related appointments are cancelled because of a shared health event. For example, the EHR 315 may include information about the cancelled appointment and the type of treatment or health-related need associated with the cancelled appointment for a patient. It may be possible that not every patient health record included in the EHR 315 is related to a cancelled health-related appointment because of the shared health event. As such, the patient identification module 410 may be configured to evaluate each of the patient health records in the EHR 315 to identify those patient health records that are related to cancelled health-related appointments. The information about these patients may be stored as patients with cancelled health-related appointments 420.

Figure 4B:
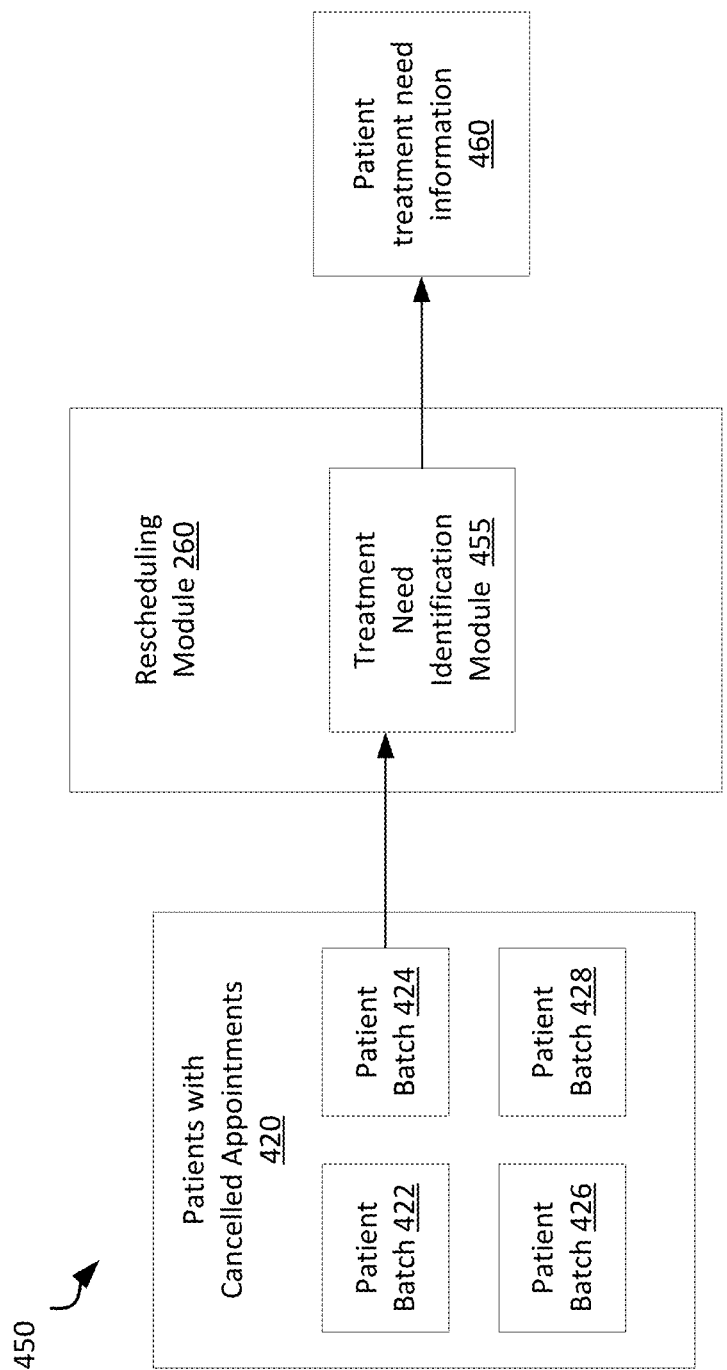
FIG. 4B shows an example rescheduling module with its treatment need identification operation, in accordance with some implementations.

FIG. 4B shows an example rescheduling module with its treatment need identification operation, in accordance with some implementations. As shown in diagram 450, the rescheduling module 260 may be configured to include a treatment need identification module 455. The treatment needs associated with the cancelled appointments may vary with each patient. For some implementations, the treatment need identification module 455 may be configured to evaluate the patient record of each of the patients with the cancelled appointments 420 and determine the treatment need associated with the cancelled appointments. For example, one patient's cancelled appointment may be related to removing kidney stones, while another patient's cancelled appointment may be related to a colonoscopy.

For some implementations, instead of evaluating the patient record of all of the patients with the cancelled appointments 420, the treatment need identification module 455 may be configured to evaluate the patients with the cancelled appointments 420 in different batches. The number of patients in a batch may be a subset of the all the patients with the cancelled appointments 420. For example, the number of patients with cancelled appointments may be divided into four different patient batches 422, 424, 426 and 428.

Figure 6A:
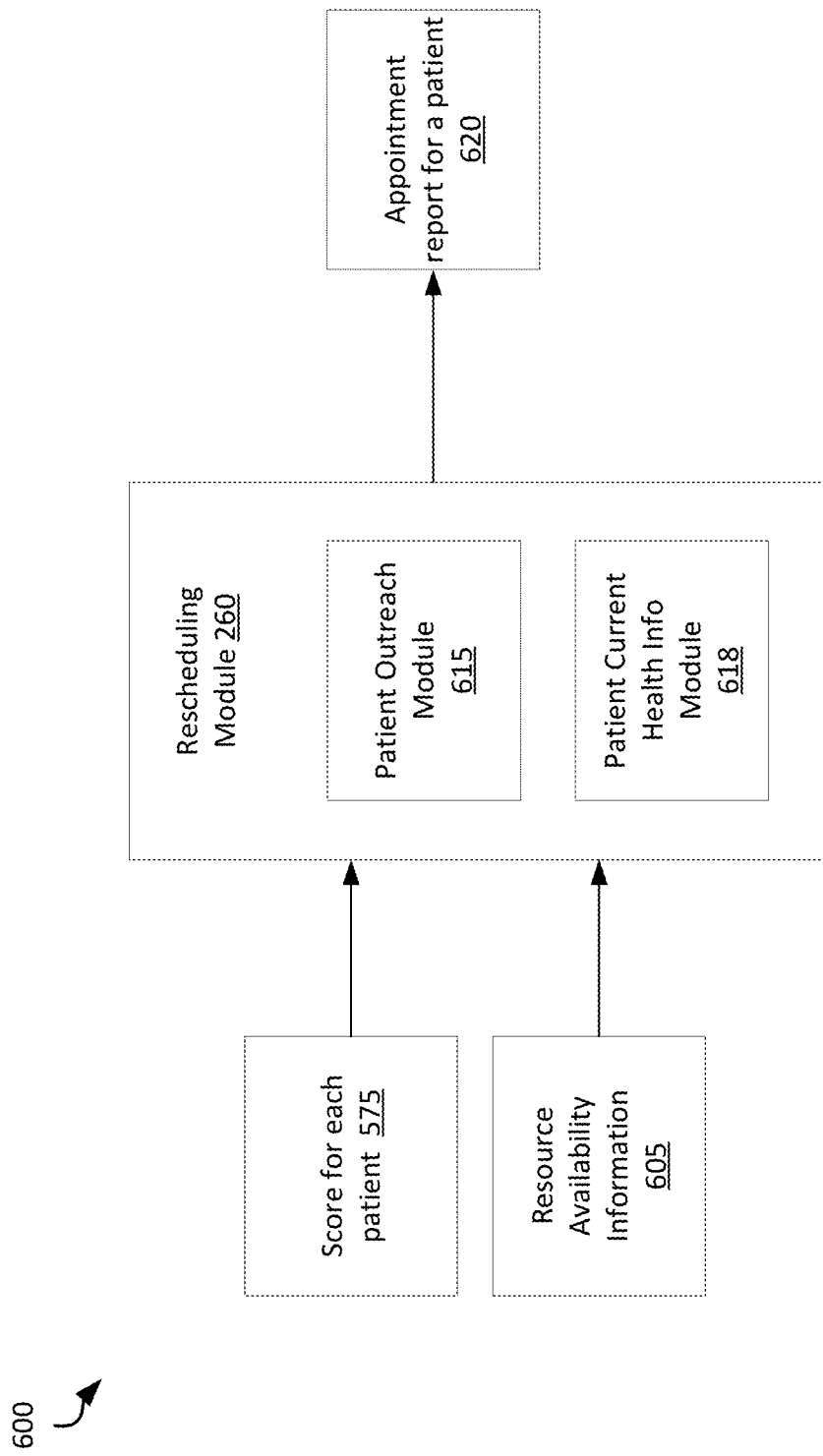
FIG. 6A shows an example patient outreach module, in accordance with some implementations.

For some implementations, the treatment need identification module 455 may be configured to evaluate the patients one batch at a time. For example, the patient batch 422 may be evaluated first, and appointments may be scheduled for the patient batch 422 (as shown in FIG. 6A) before the patient batches 424, 426 and 428 are evaluated. For example, the patient treatment need information 460 may correspond to the patient batch 422.

For some implementations, the size of a patient batch to be evaluated may vary based on the current reopening phase. For example, the size of a patient batch may be smaller (such as 20 patients) during an earlier reopening phase (such as phase 2 in New York) of the shared-health event as compared to the size of a patient batch (such as 200 patients) to be evaluated during a later reopening phase (such as phase 3 in New York) of the shared health event. For some implementations, there may be evaluations of multiple patient batches during the same reopening phase. For example, both patient batches 422 and 424 may be evaluated during phase 2 in New York, and patient batches 426 and 428 may be evaluated during phase 2 in New York.

Figure 5A:
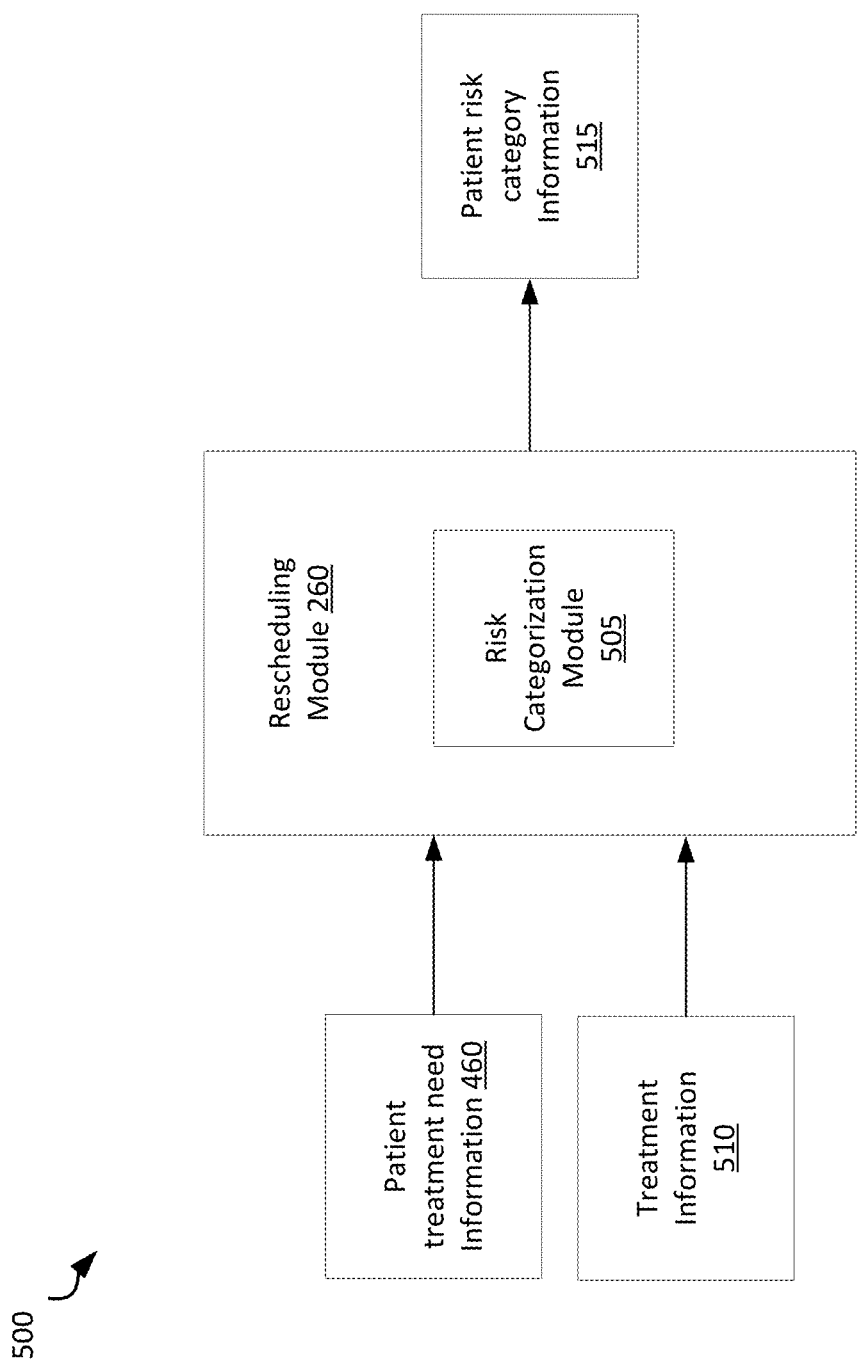
FIG. 5A shows an example rescheduling module with its risk categorizing operations, in accordance with some implementations.

FIG. 5A shows an example rescheduling module with its risk categorizing operations, in accordance with some implementations. As shown in diagram 500, the rescheduling module 260 may be configured to include a risk categorization module 505. The risk categorization module 505 may be configured to receive the patient treatment or health-related need information 460 and treatment information 510. For some implementations, the risk categorization module 505 may be configured to use the treatment information 510 to categorize the treatment or health-related needs into different risk categories. A risk category may be used to refer to the risk to the health of the patient if treatment is delayed. For example, some patients may need immediate attention because of the potential high risk associated with their treatment needs, while some other patients may need less immediate attention because of the potential low risk associated with their treatment needs.

The treatment information 510 may be established based on prior experience treating patients having similar treatment needs or based on recommendation of experts in the same field. For example, the treatment information 510 may include information indicating a colonoscopy is a low-risk category and a chemotherapy treatment is a high-risk category. The treatment information 510 may include information regarding the type of lab tests that may be required for the different types of treatment needs. Based on the patient treatment need information 460 and the treatment information 510, the risk categorization module 505 may assign a risk category to each patient. There may be many different risk categories ranging from a lowest risk to a highest risk. For example, there may be a low risk, a medium risk and a high risk. The risk categories of the patients may be stored in the patient risk category information 515. For some implementations, the risk category associated with each of the patients may be used to prioritize the patients that may need to be rescheduled for return appointments and the procedures and resources that may be required to treat the patients during their return appointments.

Figure 5B:
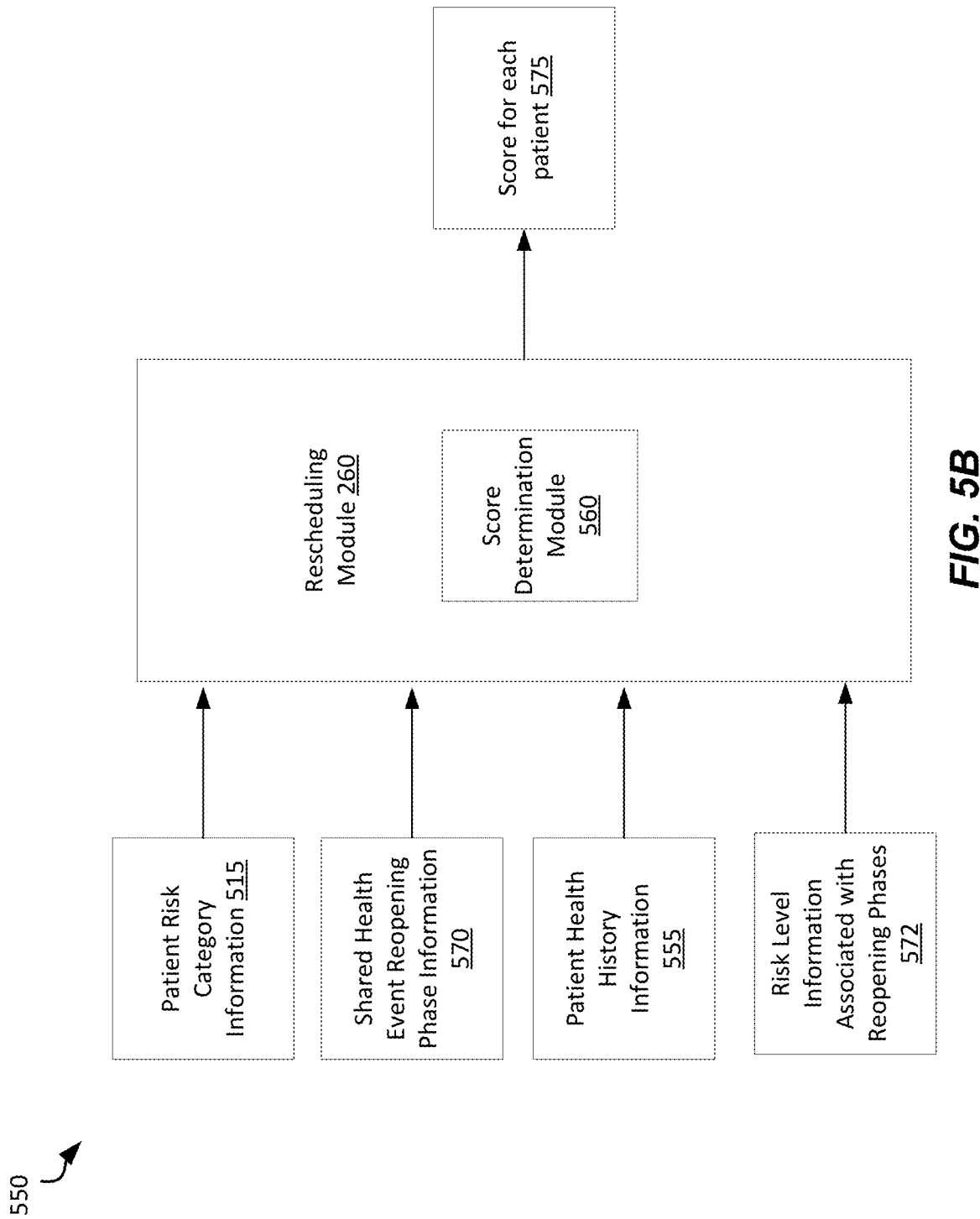
FIG. 5B shows an example rescheduling module with its score determination operations, in accordance with some implementations.

FIG. 5B shows an example rescheduling module with its score determination operations, in accordance with some implementations. As shown in diagram 550, the rescheduling module 260 may be configured to include a score determination module 560. The score determination module 560 may be configured to receive the patient risk category information 515 and patient health history information 555. The patient health history information 555 may be accessed from the EHR 315 (shown in FIG. 3A). For some implementations, the score determination module 560 may be configured to evaluate the patient health history information 555 for each patient associated with the patient risk category information 515. Evaluating the patient health history information 555 for a patient may include evaluating the patient's prior treatments. For some implementations, evaluating the patient health history information 555 for a patient may also include determining a patient's characteristic which may include one or more of the patient's age, ethnic background, gender and geographic location where the patient is residing. For example, a patient who is healthy and associated with a high-risk category may be able to return for an appointment earlier than a patient who is not healthy and associated with a low-risk category.

For some implementations, the score determination module 560 may be configured to receive shared health event reopening phase information 570 for a particular geographical area where the patients are being evaluated for return appointments. For example, the score determination module 560 may be configured to evaluate patients in New York and, based on a current date, it may be able to determine a current reopening phase from the shared health event reopening phase information 570 for New York. For some implementations, the score determination module 560 may be configured to receive the risk level information associated with the reopening phases 572. For example, New York may consider the risk level associated with the reopening phase 1 to be highest, and the risk level associated with the reopening phase 3 to be lowest. For some implementations, the score determination module 560 may be configured to combine the risk level associated with a current reopening phase and the risk category associated with a patient to generate a combined score (or score) for each patient 575. For example, a patient assigned with a higher score may be able to return for an appointment sooner than a patient with a patient assigned with a lower score.

FIG. 5C shows an example score table generated using the risk categories for a patient and the risk level associated with reopening phases, in accordance with some implementations. The score table 680 includes the different reopening phases along the columns in decreasing risk level and the different risk categories along the row in decreasing risk categories. The content of each cell of the table may represent a score. In this example, the scores may range from "1" to "4". A score of "1" may indicate that the situation is too dangerous to schedule a patient for a return appointment, and a score of "4" may indicate that the situation is sufficiently safe to schedule a patient for a return appointment. A score of "2" and "3" may be safe for some patients but may not be safe for others. For example, a patient assigned with a category 1 (as determined by the risk categorization module 505 shown in FIG. 5A) may be given a score of "1" (by the score determination module 560 shown in FIG. 5B) when the current reopening phase is the first phase. Similarly, a patient assigned with a category 2 may be given a score of "2" when the current reopening phase is the third phase; a patient assigned with a category 3 may be given a score of "2" when the current reopening phase is the second phase, and a patient assigned with a category 4 may be given a score of "3" when the current reopening phase is the second phase or third phase and a score of "4" when the current reopening phase is the fourth phase. It may be noted that other score values may be used to reflect a score of a patient based on the patient's risk category and a current reopening phase.

For some implementations, the healthcare system 305 may be configured to correlate the characteristic information about the patients, their treatment needs and their scores (as determined by the score determination module 560) to derive at treatment plans or resource allocation plans that may be applicable to different communities or different population groups in a community. As more data is collected, patterns may be established from the outcome of the correlation operations. The patterns may be analyzed to learn about coping with changes in the community with respect to a certain health condition and population groups. For example, using the characteristic information, the correlation may be performed based on one or more of gender, ethnicity, race, age group and geographical areas. When available, other characteristic information may also be used including, for example, education background, income, etc. An example of a population group may be all male patients between the age of 45 and 65. An example of a pattern may be males of European origin are more likely to have high blood pressure if they live on the West coast of the United States. The correlation may be performed on a continuous basis based on existing data as well as data collected on new patients added to the EHR 315. This may be useful to organizations (e.g., hospitals) associated with the healthcare system 305 in terms of managing available resources to provide more efficient services to the patients. This may also be useful in driving operational efficiency in both hospital and surgical facilities.

It may be possible that a shared health event may include multiple waves before a vaccine is discovered and become widely available. For some implementations, the scores (as determined by the score determination module 560) may be stored in the EHR 315 for each patient. For some implementations, as the scores are stored in the EHR 315 for multiple geographical areas (e.g., by regions, states, zip codes, etc.), it may be possible to use the information stored in the EHR 315 to identify or predict a next wave of shared-health event by geographical area based on information collected from the patients during engagement by the patient outreach module 615. For example, when a patient is engaged for a return appointment, feedback may be received from the patient that the patient is experiencing some symptoms that do not allow the patient to commit to a return appointment. The patient's current health condition may be noted in the HER 315. When there are a high number of patients in a geographical area complaining about similar symptoms, it is possible that an outbreak (or another wave of a pandemic) may be happening in the geographical area.

FIG. 6A shows an example patient outreach module, in accordance with some implementations. In diagram 600, the rescheduling module 260 may include patient outreach module 615 and may be configured to engage with a plurality of patents and schedule the plurality of patients for return appointments. For some implementations, the patient outreach module 615 may be coupled with patient current health information module 618.

For some implementations, the patient outreach module 615 may be configured to receive the score for each patient 575 (also shown in FIG. 5B) and schedule the return appointments for each patient based on the patient's score. For example, a patient with a high score may be scheduled for a return appointment prior to a patient with a lower score.

For some implementations, the patient outreach module 615 may be configured to receive resource availability information 605 and may take into consideration of the resource availability when scheduling a patient for a return appointment. For example, a surgery that requires a patient to stay in the hospital for two days post-surgery may not be scheduled when the hospital does not have a bed to accommodate the patient. As another example, a surgery that requires a heart specialist at one hospital may not be scheduled when the heart specialist is already scheduled to be at another hospital. When the appointments are confirmed and scheduled with the patients, the patient outreach module 615 may then generate an appointment report 620 that includes all the return appointments. It may be noted that the appointment report 620 may include information about patients not scheduled for a return appointment because those patients are experiencing symptoms that may be associated with an infection of the shared health event.

For some implementations, the patient outreach module 615 may be configured to evaluate the risk of the patients not showing up for the return appointments. For example, this may be determined based on past activities of the patients as related to missing appointments. For some implementations, the patient outreach module 615 may be configured to perform reminder operations to remind the patients who have past histories of missing appointments. The reminder may be sent to a computing device associated with the patient. This may help reducing costs associated with missing appointments and a timely confirmation of a potential missing appointment may enable the patient outreach module 615 to find a replacement patient from the patients with cancelled appointments 420.

For some implementations, the patient outreach module 615 may be configured to include self-service operations to enable the patients to communicate information that may be used to schedule the return appointments. For example, the patients may use a computing device to use the self-help service to respond to questions about their availability for the return appointments as well as any other information that may be used to accommodate the patients for the return appointments.

For some implementations, the patient current health information module 618 may be configured to request for the current health information of a patient. The patient current health information module 619 may be configured to generate and present questions to the patient to determine if a patient has symptoms that may be related certain illness. For example, questions related to symptoms consistent with the symptoms of a shared health event may be communicated to a computer system (e.g., smart phone) associated with the patient. For some implementations, warnings may be generated by the patient current health information module 618 based on the symptoms received from a patient. For example, the warnings may be generated when the symptoms reported by a patient are consistent with the symptoms of a shared health event such as a pandemic.

Figure 6B:
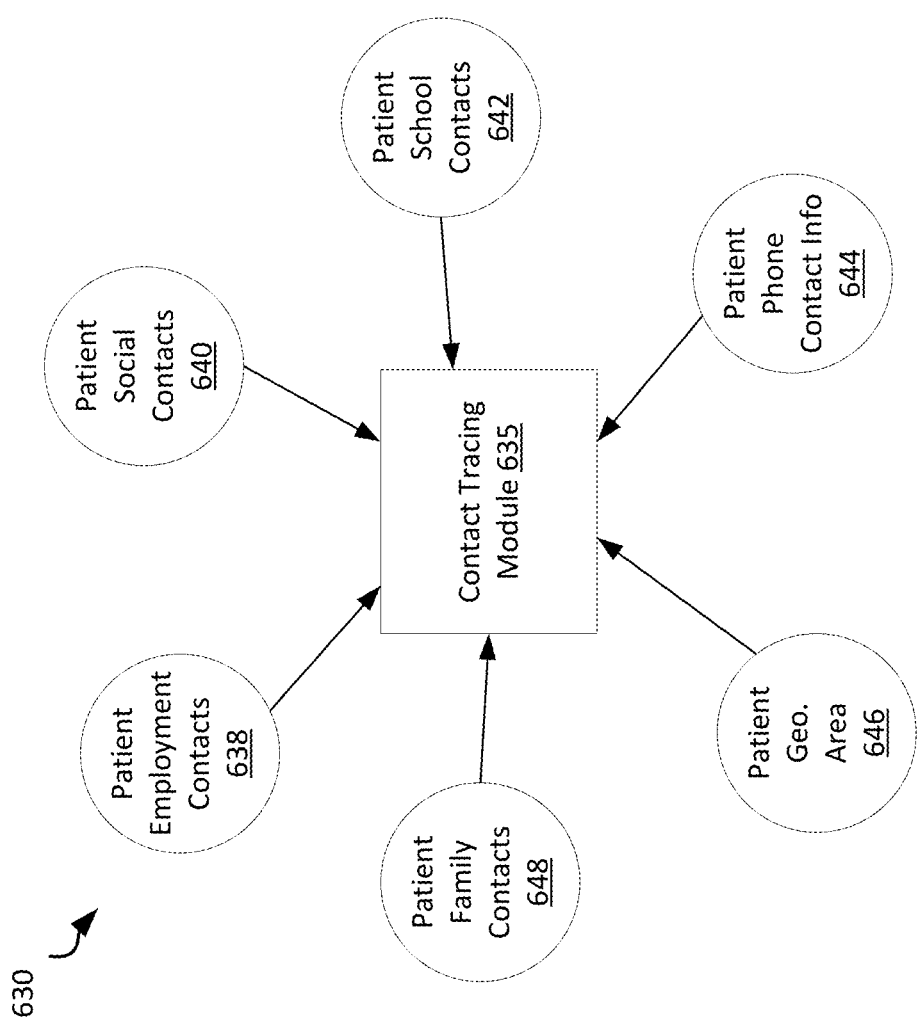
FIG. 6B shows an example of a contact tracing module, in accordance with some implementations.

FIG. 6B shows an example of a contact tracing module, in accordance with some implementations. Diagram 630 includes contact tracing module 635 which may be coupled with patient current health information module 618 (shown in FIG. 6A). For some implementations, the contact tracing module 635 may be included in the rescheduling module 260. The patient current health information module 618 may be configured to determine contact information associated with a patient. For some implementations, when warnings are generated based on the symptoms received from a patient, the contact information may be used by the contact tracing module 635 to perform contact tracing. This may include sending a series of questions to the people identified by the contact information to verify potential infectivity. This process may be repeated when an infectivity is confirmed until a specified number of outreaches is performed. For some implementations, when a certain number of people are identified as having the same infection as a patient evaluated by the rescheduling module 260, an outbreak may be declared.

For some implementations, the contact information used to perform contact tracing may be categorized as patient employment contacts 638, patient social contacts 640, patient school contacts 642, patient phone contact information 644, patient geographical area 646 and patient family contacts 648.

The patient employment contacts 638 may include contact information about people that a patient may have contact with during employment. For example, this may include colleagues and clients. For some implementations, the patient employment contacts 638 may be determined by communicating with a computer system associated with the patient's place of employment. The patient social contacts 640 may include contact information about people that the patient may have contact with during social events. For example, this may include people attending the same party or movie theater. For some implementations, the patient social contacts 640 may be determined from the patient's electronic calendar via the patient's smart phone.

The patient school contacts 642 may include contact information about people that the patient may come across while being at the schools. For example, this may include people attending the same class or being in the same classroom as the patient. For some implementations, the patient school contacts 642 may be determined by communicating with a computer system associated with the school. The patient phone contact information 644 may include contacts saved in the patient's smart phone. For example, this may include the patient's friends and associates that may not be identified in the other categories.

The patient geographical area 646 may include contact information about people that are near the location where the patient lives or locations where the patient has recently been to. For some implementations, the patient geographical area 646 may be determined from Global Positioning System (GPS) information recorded by the patient's personal computing device (e.g., smart phone). For some implementations, this may include reviewing the patient's credit card transactions to determine the physical location where the credit card transactions occur. The patient family contacts 646 may include contact information about the patient's relatives. For example, this may include contact information of immediate family members such as spouse and children. For some implementations, the patient family contacts 646 may be determined from the patient's electronic medical record.

Figure 6C:
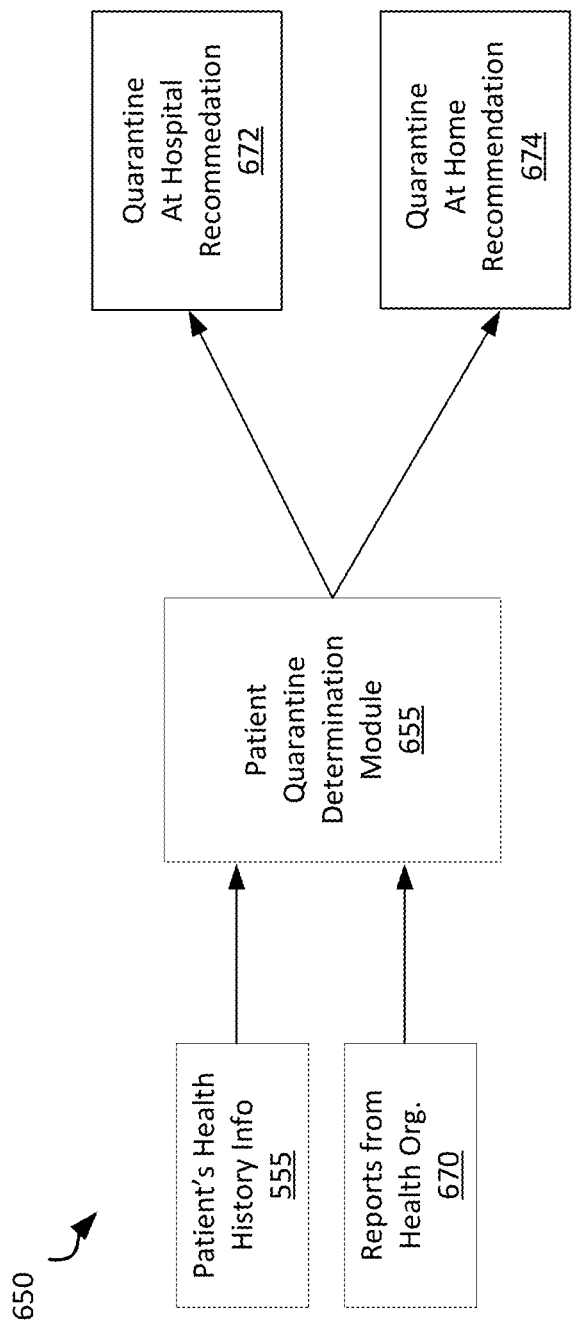
FIG. 6C shows an example of a quarantine determination module, in accordance with some implementations.

FIG. 6C shows an example of a quarantine determination module, in accordance with some implementations. Diagram 650 includes quarantine determination module 655 which may be coupled with the contact tracing module 635 (shown in FIG. 6B). For some implementations, the quarantine determination module 655 may be included in the rescheduling module 260. The quarantine determination module 655 may be configured to evaluate an infected patient. The quarantine determination module 655 may be configured to receive a patient's health history information 555 and reports from governmental health organizations 670 to generate recommendation about how an infected patient should be quarantined. For example, the governmental health organization may be the U.S. Department of Health & Human Services. According to the Centers for Disease Control and Prevention (CDC) which is an agency under the U.S. Department of Health & Human Services, people at any age with certain underlying conditions may be at increased risk of severe illness from COVID-19. These underlying conditions may include Cancer, Chronic kidney disease, COPD (chronic obstructive pulmonary disease), Immunocompromised state (weakened immune system) from solid organ transplant, Obesity (body mass index [BMI] of 30 or higher), Serious heart conditions, such as heart failure, coronary artery disease, or cardiomyopathies, Sickle cell disease and Type 2 diabetes mellitus. As such, when the patient's health history information 555 shows one of the underlying conditions identified by the governmental health organization, a quarantine at a hospital recommendation 672 may be generated. Otherwise, a quarantine at home recommendation 674 may be generated.

For some implementations, when a quarantine at a hospital recommendation 672 is generated, the rescheduling module 260 (shown in FIG. 6A) may be configured to evaluate the resource availability information 605 (also shown in FIG. 6A) to determine a hospital or a healthcare facility that has sufficient resources to receive and keep a patient under quarantine. For some implementations, operations performed by the rescheduling module 260 for infected patients may be collected and evaluated based on various factors (e.g., age, gender, etc.) to generate a predictive outcome for a specified population or geography to anticipate and keep potential outbreak under control.

Figure 7:
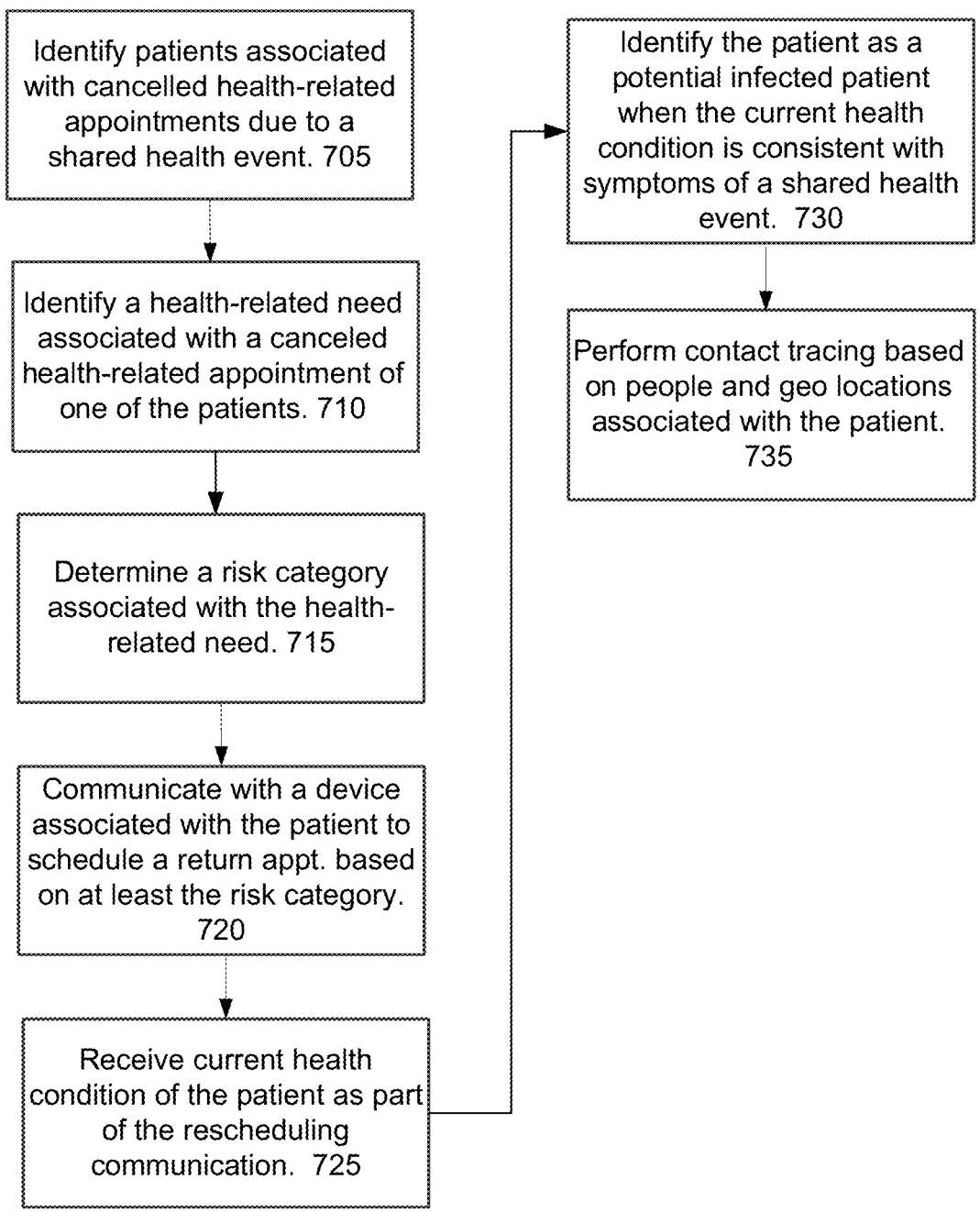
FIG. 7 is an example flow diagram of a process that may be used identify potential infected patients, in accordance with some implementations.

FIG. 7 is an example flow diagram of a process that may be used identify potential infected patients, in accordance with some implementations. The process may be performed by a healthcare system and related modules and diagrams shown in FIGS. 3A to 6C.

At block 705, the patients whose healthcare appointments were cancelled due to a shared health event are identified. This may require accessing an EHR such as the EHR 315 described in FIG. 3A. At block 710, the treatment or health-related need associated with each patient may be identified. For example, a treatment need may be a colonoscopy. At block 715, a risk category may be associated with a patient based on the patient's treatment need and treatment information. For example, a colonoscopy may be considered a low-risk operation, while a cancer-related surgery may be considered a high-risk operation.

At block 720, the patient may be contacted to schedule a return appointment. The contact may be made based at least on the patient's risk category. The contact may also be made based on a current reopening phase. Contact with a patient may be made via a device such as a smart phone associated with the patient.

At block 725, inquiries may be sent to the patients to determine a patient's current health situation. It's possible that a patient may not be healthy enough to schedule for a return appointment. Information about a patient's current health condition may include any symptoms that the patient may experience at a current time or, for example, within the previous several days.

At block 730, when the symptoms experienced by the patient are consistent with the symptoms associated with a shared health event, the patient may be identified as a potential infected patient. At block 735, when a patient is a potentially infected patient, contact tracing may be performed based on the people that the patient may have contact with and based on locations that the patient may have been to recently. For some implementations, the contact tracing may be performed based on while the patient experiences the symptoms.

Figure 8A:
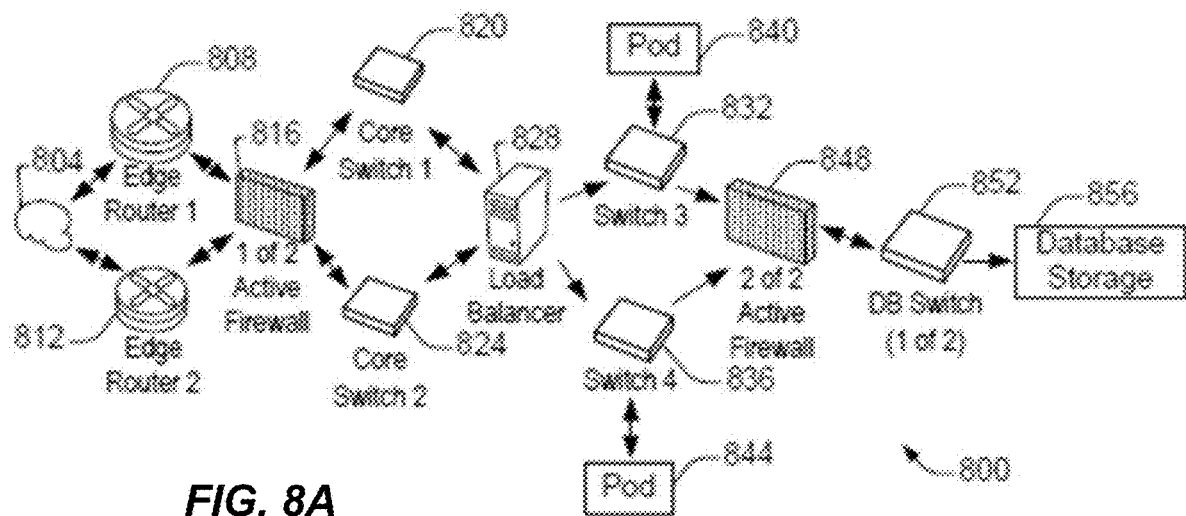
FIG. 8A shows a system diagram illustrating architectural components of an applicable environment, in accordance with some implementations.

FIG. 8A shows a system diagram 800 illustrating architectural components of an on-demand service environment, in accordance with some implementations. A client machine located in the cloud 804 (or Internet) may communicate with the on-demand service environment via one or more edge routers 808 and 812. The edge routers may communicate with one or more core switches 820 and 824 via firewall 816. The core switches may communicate with a load balancer 828, which may distribute server load over different pods, such as the pods 840 and 844. The pods 840 and 844, which may each include one or more servers and/or other computing resources, may perform data processing and other operations used to provide on-demand Services. Communication with the pods may be conducted via pod switches 832 and 836. Components of the on-demand service environment may communicate with a database storage system 856 via a database firewall 848 and a database switch 852.

Figure 8B:
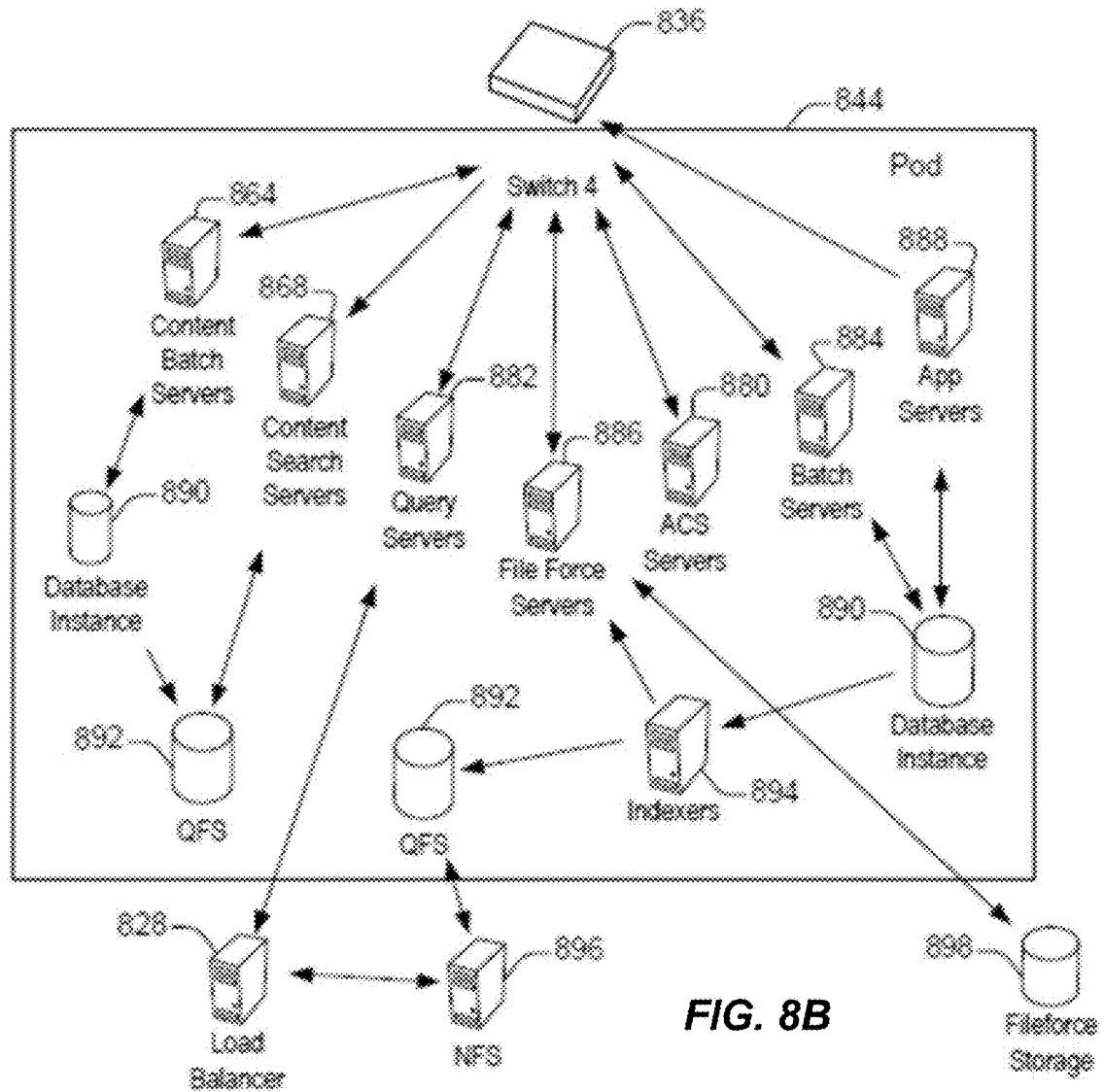
FIG. 8B shows a system diagram further illustrating architectural components of an applicable environment, in accordance with some implementations.

As shown in FIGS. 8A and 8B, accessing an on-demand service environment may involve communications transmitted among a variety of different hardware and/or software components. Further, the on-demand service environment 800 is a simplified representation of an actual on-demand service environment. For example, while only one or two devices of each type are shown in FIGS. 8A and 8B, some implementations of an on-demand service environment may include anywhere from one to many devices of each type. Also, the on-demand service environment need not include each device shown in FIGS. 8A and 8B or may include additional devices not shown in FIGS. 8A and 8B.

Moreover, one or more of the devices in the on-demand service environment 800 may be implemented on the same physical device or on different hardware. Some devices may be implemented using hardware or a combination of hardware and software. Thus, terms such as "data processing apparatus," "machine," "server" and "device" as used herein are not limited to a single hardware device, but rather include any hardware and software configured to provide the described functionality.

The cloud 804 is intended to refer to a data network or plurality of data networks, often including the Internet. Client machines located in the cloud 804 may communicate with the on-demand service environment to access services provided by the on-demand service environment. For example, client machines may access the on-demand service environment to retrieve, store, edit, and/or process information.

In some implementations, the edge routers 808 and 812 route packets between the cloud 804 and other components of the on-demand service environment 800. The edge routers 808 and 812 may employ the Border Gateway Protocol (BGP). The BGP is the core routing protocol of the Internet. The edge routers 808 and 812 may maintain a table of IP networks or 'prefixes' which designate network reachability among autonomous systems on the Internet.

In one or more implementations, the firewall 816 may protect the inner components of the on-demand service environment 800 from Internet traffic. The firewall 816 may block, permit, or deny access to the inner components of the on-demand service environment 800 based upon a set of rules and other criteria. The firewall 816 may act as one or more of a packet filter, an application gateway, a stateful filter, a proxy server, or any other type of firewall.

In some implementations, the core switches 820 and 824 are high-capacity switches that transfer packets within the on-demand service environment 800. The core switches 820 and 824 may be configured as network bridges that quickly route data between different components within the on-demand service environment. In some implementations, the use of two or more core switches 820 and 824 may provide redundancy and/or reduced latency.

In some implementations, the pods 840 and 844 may perform the core data processing and service functions provided by the on-demand service environment. Each pod may include various types of hardware and/or software computing resources. An example of the pod architecture is discussed in greater detail with reference to FIG. 8B.

In some implementations, communication between the pods 840 and 844 may be conducted via the pod switches 832 and 836. The pod switches 832 and 836 may facilitate communication between the pods 840 and 844 and client machines located in the cloud 804, for example via core switches 820 and 824. Also, the pod switches 832 and 836 may facilitate communication between the pods 840 and 844 and the database storage 856.

In some implementations, the load balancer 828 may distribute workload between the pods 840 and 844. Balancing the on-demand service requests between the pods may assist in improving the use of resources, increasing throughput, reducing response times, and/or reducing overhead. The load balancer 828 may include multilayer switches to analyze and forward traffic.

In some implementations, access to the database storage 856 may be guarded by a database firewall 848. The database firewall 848 may act as a computer application firewall operating at the database application layer of a protocol stack. The database firewall 848 may protect the database storage 856 from application attacks such as structure query language (SQL) injection, database rootkits, and unauthorized information disclosure.

In some implementations, the database firewall 848 may include a host using one or more forms of reverse proxy services to proxy traffic before passing it to a gateway router. The database firewall 848 may inspect the contents of database traffic and block certain content or database requests. The database firewall 848 may work on the SQL application level atop the TCP/IP stack, managing applications' connection to the database or SQL management interfaces as well as intercepting and enforcing packets traveling to or from a database network or application interface.

In some implementations, communication with the database storage system 856 may be conducted via the database switch 852. The multi-tenant database system 856 may include more than one hardware and/or software components for handling database queries. Accordingly, the database switch 852 may direct database queries transmitted by other components of the on-demand service environment (e.g., the pods 840 and 844) to the correct components within the database storage system 856. In some implementations, the database storage system 856 is an on-demand database system shared by many different organizations. The on-demand database system may employ a multi-tenant approach, a virtualized approach, or any other type of database approach. An on-demand database system is discussed in greater detail with reference to FIGS. 9 and 10.

FIG. 8B shows a system diagram illustrating the architecture of the pod 844, in accordance with one implementation. The pod 844 may be used to render services to a user of the on-demand service environment 800. In some implementations, each pod may include a variety of servers and/or other systems. The pod 844 includes one or more content batch servers 864, content search servers 868, query servers 882, Fileforce servers 886, access control system (ACS) servers 880, batch servers 884, and app servers 888. Also, the pod 844 includes database instances 890, quick file systems (QFS) 892, and indexers 894. In one or more implementations, some or all communication between the servers in the pod 844 may be transmitted via the switch 836.

In some implementations, the application servers 888 may include a hardware and/or software framework dedicated to the execution of procedures (e.g., programs, routines, scripts) for supporting the construction of applications provided by the on-demand service environment 800 via the pod 844. Some such procedures may include operations for providing the services described herein. The content batch servers 864 may request internal to the pod. These requests may be long-running and/or not tied to a particular customer. For example, the content batch servers 864 may handle requests related to log mining, cleanup work, and maintenance tasks.

The content search servers 868 may provide query and indexer functions. For example, the functions provided by the content search servers 868 may allow users to search through content stored in the on-demand service environment. The Fileforce servers 886 may manage requests information stored in the Fileforce storage 898. The Fileforce storage 898 may store information such as documents, images, and basic large objects (BLOBs). By managing requests for information using the Fileforce servers 886, the image footprint on the database may be reduced.

The query servers 882 may be used to retrieve information from one or more file systems. For example, the query system 872 may receive requests for information from the app servers 888 and then transmit information queries to the NFS 896 located outside the pod. The pod 844 may share a database instance 890 configured as a multi-tenant environment in which different organizations share access to the same database. Additionally, services rendered by the pod 844 may require various hardware and/or software resources. In some implementations, the ACS servers 880 may control access to data, hardware resources, or software resources.

In some implementations, the batch servers 884 may process batch jobs, which are used to run tasks at specified times. Thus, the batch servers 884 may transmit instructions to other servers, such as the app servers 888, to trigger the batch jobs. For some implementations, the QFS 892 may be an open source file system available from Sun Microsystems® of Santa Clara, California. The QFS may serve as a rapid-access file system for storing and accessing information available within the pod 844. The QFS 892 may support some volume management capabilities, allowing many disks to be grouped together into a file system. File system metadata can be kept on a separate set of disks, which may be useful for streaming applications where long disk seeks cannot be tolerated. Thus, the QFS system may communicate with one or more content search servers 868 and/or indexers 894 to identify, retrieve, move, and/or update data stored in the network file systems 896 and/or other storage systems.

In some implementations, one or more query servers 882 may communicate with the NFS 896 to retrieve and/or update information stored outside of the pod 844. The NFS 896 may allow servers located in the pod 844 to access information to access files over a network in a manner similar to how local storage is accessed. In some implementations, queries from the query servers 882 may be transmitted to the NFS 896 via the load balancer 820, which may distribute resource requests over various resources available in the on-demand service environment. The NFS 896 may also communicate with the QFS 892 to update the information stored on the NFS 896 and/or to provide information to the QFS 892 for use by servers located within the pod 844.

In some implementations, the pod may include one or more database instances 890. The database instance 890 may transmit information to the QFS 892. When information is transmitted to the QFS, it may be available for use by servers within the pod 844 without requiring an additional database call. In some implementations, database information may be transmitted to the indexer 894. Indexer 894 may provide an index of information available in the database 890 and/or QFS 892. The index information may be provided to Fileforce servers 886 and/or the QFS 892.

Figure 9:
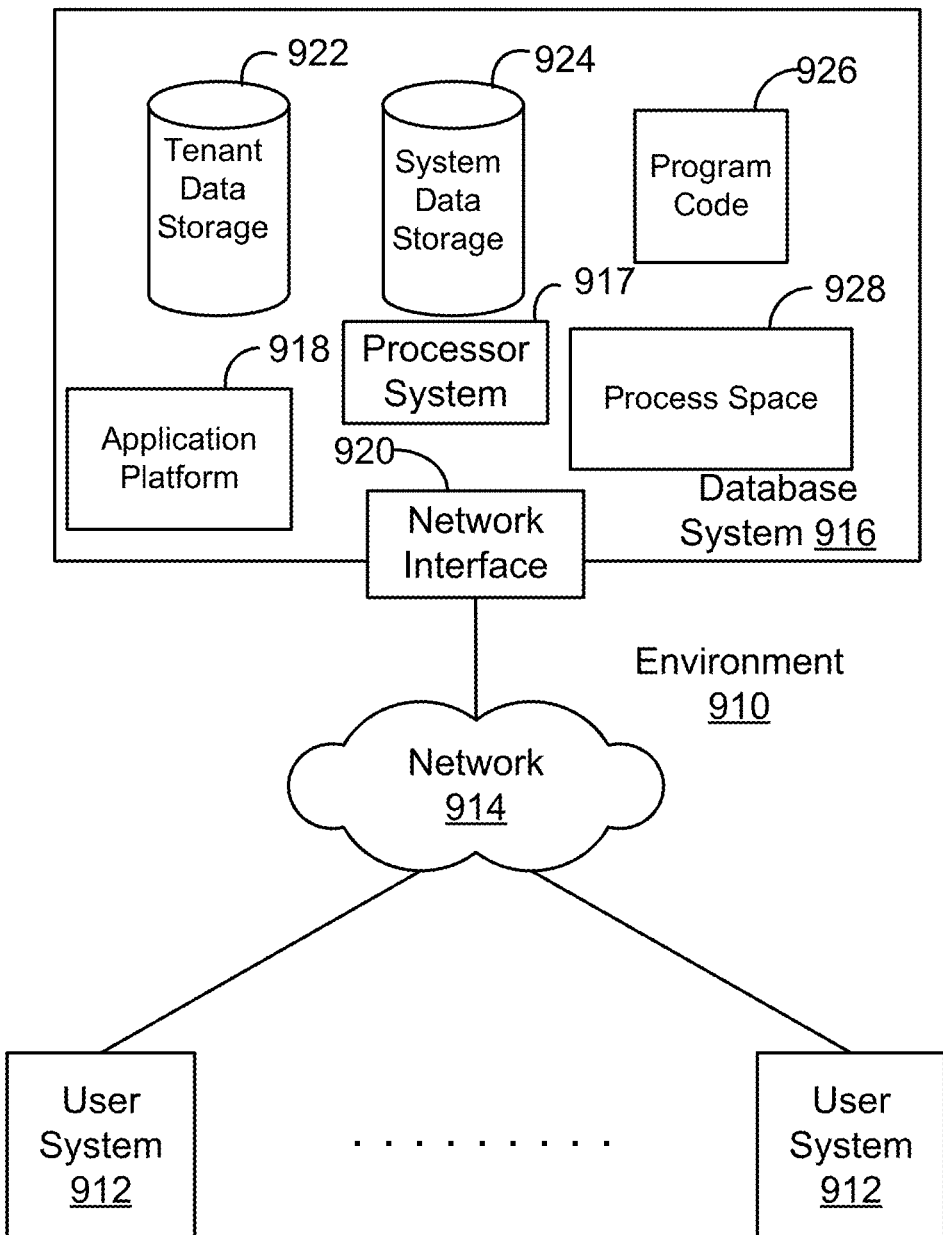
FIG. 9 shows a system diagram illustrating the architecture of a multi-tenant database environment, in accordance with some implementations.
Figure 10:
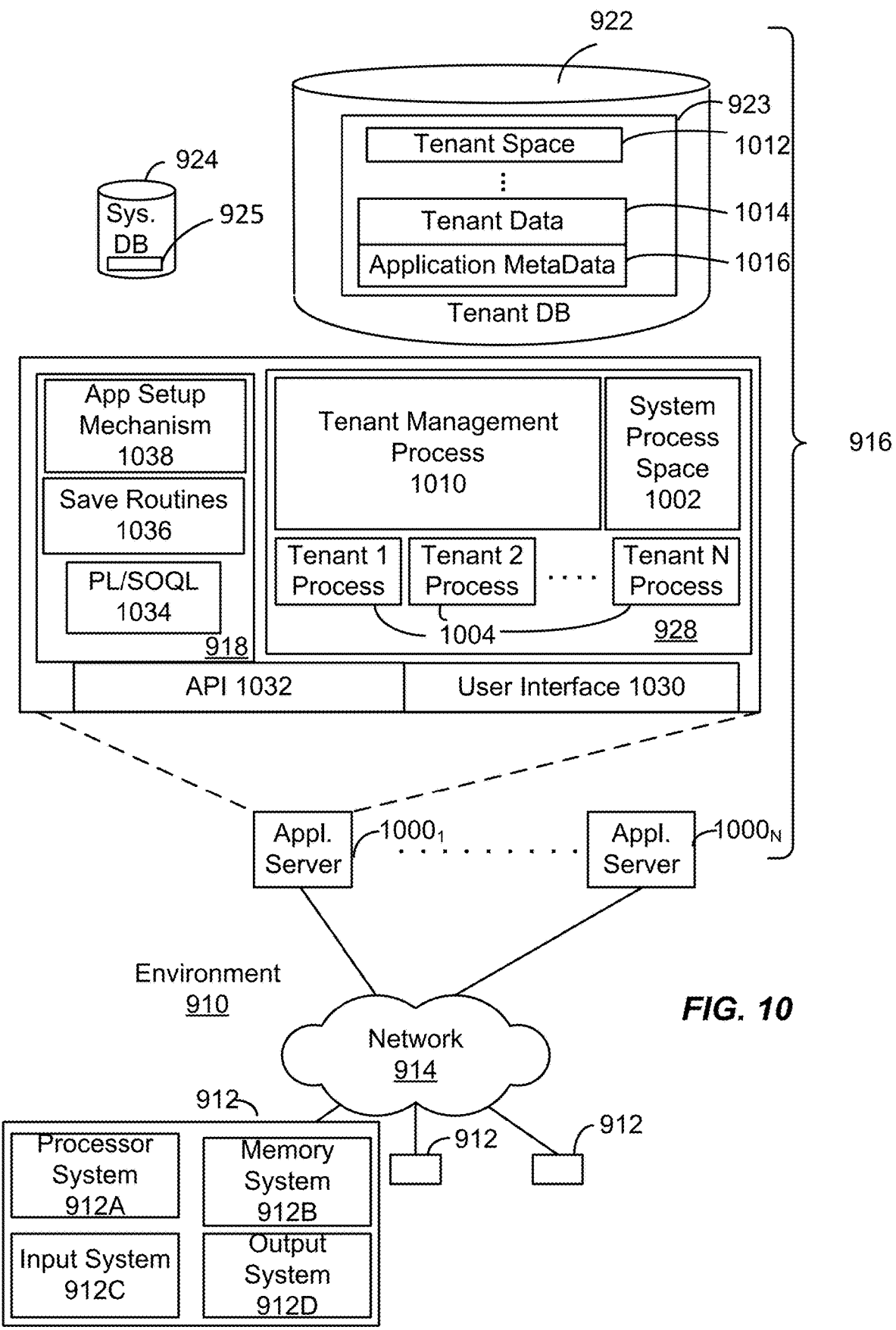
FIG. 10 shows a system diagram further illustrating the architecture of a multi-tenant database environment, in accordance with some implementations.

FIG. 9 shows a block diagram of an environment 910 wherein an on-demand database service might be used, in accordance with some implementations. Environment 910 includes an on-demand database service 916. User system 912 may be any machine or system that is used by a user to access a database user system. For example, any of user systems 912 can be a handheld computing system, a mobile phone, a laptop computer, a workstation, and/or a network of computing systems. As illustrated in FIGS. 9 and 10, user systems 912 might interact via a network 914 with the on-demand database service 916.

An on-demand database service, such as system 916, is a database system that is made available to outside users that do not need to necessarily be concerned with building and/or maintaining the database system, but instead may be available for their use when the users need the database system (e.g., on the demand of the users). Some on-demand database services may store information from one or more tenants stored into tables of a common database image to form a multi-tenant database system (MTS). Accordingly, "on-demand database service 916" and "system 916" will be used interchangeably herein. A database image may include one or more database objects. A relational database management system (RDBMS) or the equivalent may execute storage and retrieval of information against the database object(s). Application platform 918 may be a framework that allows the applications of system 916 to run, such as the hardware and/or software, e.g., the operating system. In an implementation, on-demand database service 916 may include an application platform 918 that enables creation, managing and executing one or more applications developed by the provider of the on-demand database service, users accessing the on-demand database service via user systems 912, or third party application developers accessing the on-demand database service via user systems 912.

One arrangement for elements of system 916 is shown in FIG. 9, including a network interface 920, application platform 918, tenant data storage 922 for tenant data 923, system data storage 924 for system data 925 accessible to system 916 and possibly multiple tenants, program code 926 for implementing various functions of system 916, and a process space 928 for executing MTS system processes and tenant-specific processes, such as running applications as part of an application hosting service. Additional processes that may execute on system 916 include database indexing processes.

The users of user systems 912 may differ in their respective capacities, and the capacity of a particular user system 912 might be entirely determined by permissions (permission levels) for the current user. For example, where a call center agent is using a particular user system 912 to interact with system 916, the user system 912 has the capacities allotted to that call center agent. However, while an administrator is using that user system to interact with system 916, that user system has the capacities allotted to that administrator. In systems with a hierarchical role model, users at one permission level may have access to applications, data, and database information accessible by a lower permission level user, but may not have access to certain applications, database information, and data accessible by a user at a higher permission level. Thus, different users may have different capabilities with regard to accessing and modifying application and database information, depending on a user's security or permission level.

Network 914 is any network or combination of networks of devices that communicate with one another. For example, network 914 can be any one or any combination of a LAN (local area network), WAN (wide area network), telephone network, wireless network, point-to-point network, star network, token ring network, hub network, or other appropriate configuration. As the most common type of computer network in current use is a TCP/IP (Transfer Control Protocol and Internet Protocol) network (e.g., the Internet), that network will be used in many of the examples herein. However, it should be understood that the networks used in some implementations are not so limited, although TCP/IP is a frequently implemented protocol.

User systems 912 might communicate with system 916 using TCP/IP and, at a higher network level, use other common Internet protocols to communicate, such as HTTP, FTP, AFS, WAP, etc. In an example where HTTP is used, user system 912 might include an HTTP client commonly referred to as a "browser" for sending and receiving HTTP messages to and from an HTTP server at system 916. Such an HTTP server might be implemented as the sole network interface between system 916 and network 914, but other techniques might be used as well or instead. In some implementations, the interface between system 916 and network 914 includes load sharing functionality, such as round-robin HTTP request distributors to balance loads and distribute incoming HTTP requests evenly over a plurality of servers. At least as for the users that are accessing that server, each of the plurality of servers has access to the MTS' data; however, other alternative configurations may be used instead.

In some implementations, system 916, shown in FIG. 9, implements a web-based customer relationship management (CRM) system. For example, in some implementations, system 916 includes application servers configured to implement and execute CRM software applications as well as provide related data, code, forms, web pages and other information to and from user systems 912 and to store to, and retrieve from, a database system related data, objects, and Webpage content. With a multi-tenant system, data for multiple tenants may be stored in the same physical database object, however, tenant data typically is arranged so that data of one tenant is kept logically separate from that of other tenants so that one tenant does not have access to another tenant's data, unless such data is expressly shared. In certain implementations, system 916 implements applications other than, or in addition to, a CRM application. For example, system 916 may provide tenant access to multiple hosted (standard and custom) applications. User (or third party developer) applications, which may or may not include CRM, may be supported by the application platform 918, which manages creation, storage of the applications into one or more database objects and executing of the applications in a virtual machine in the process space of the system 916.

Each user system 912 could include a desktop personal computer, workstation, laptop, PDA, cell phone, or any wireless access protocol (WAP) enabled device or any other computing system capable of interfacing directly or indirectly to the Internet or other network connection. User system 912 typically runs an HTTP client, e.g., a browsing program, such as Microsoft's Internet Explorer® browser, Mozilla's Firefox® browser, Opera's browser, or a WAP-enabled browser in the case of a cell phone, PDA or other wireless device, or the like, allowing a user (e.g., subscriber of the multi-tenant database system) of user system 912 to access, process and view information, pages and applications available to it from system 916 over network 914.

Each user system 912 also typically includes one or more user interface devices, such as a keyboard, a mouse, trackball, touch pad, touch screen, pen or the like, for interacting with a graphical user interface (GUI) provided by the browser on a display (e.g., a monitor screen, LCD display, etc.) in conjunction with pages, forms, applications and other information provided by system 916 or other systems or servers. For example, the user interface device can be used to access data and applications hosted by system 916, and to perform searches on stored data, and otherwise allow a user to interact with various GUI pages that may be presented to a user. As discussed above, implementations are suitable for use with the Internet, which refers to a specific global internetwork of networks. However, it should be understood that other networks can be used instead of the Internet, such as an intranet, an extranet, a virtual private network (VPN), a non-TCP/IP based network, any LAN or WAN or the like.

According to some implementations, each user system 912 and all of its components are operator configurable using applications, such as a browser, including computer code run using a central processing unit such as an Intel Pentium® processor or the like. Similarly, system 916 (and additional instances of an MTS, where more than one is present) and all of their components might be operator configurable using application(s) including computer code to run using a central processing unit such as processor system 917, which may include an Intel Pentium® processor or the like, and/or multiple processor units.

A computer program product implementation includes a machine-readable storage medium (media) having instructions stored thereon/in which can be used to program a computer to perform any of the processes of the implementations described herein. Computer code for operating and configuring system 916 to intercommunicate and to process web pages, applications and other data and media content as described herein are preferably downloaded and stored on a hard disk, but the entire program code, or portions thereof, may also be stored in any other volatile or non-volatile memory medium or device, such as a ROM or RAM, or provided on any media capable of storing program code, such as any type of rotating media including floppy disks, optical discs, digital versatile disk (DVD), compact disk (CD), microdrive, and magneto-optical disks, and magnetic or optical cards, nanosystems (including molecular memory ICs), or any type of media or device suitable for storing instructions and/or data. Additionally, the entire program code, or portions thereof, may be transmitted and downloaded from a software source over a transmission medium, e.g., over the Internet, or from another server, or transmitted over any other conventional network connection (e.g., extranet, VPN, LAN, etc.) using any communication medium and protocols (e.g., TCP/IP, HTTP, HTTPS, Ethernet, etc.). It will also be appreciated that computer code for carrying out disclosed operations can be implemented in any programming language that can be executed on a client system and/or server or server system such as, for example, C, C++, HTML, any other markup language, Java™, JavaScript®, ActiveX®, any other scripting language, such as VBScript, and many other programming languages as are well known may be used. (Java™ is a trademark of Sun Microsystems®, Inc.).

According to some implementations, each system 916 is configured to provide web pages, forms, applications, data and media content to user (client) systems 912 to support the access by user systems 912 as tenants of system 916. As such, system 916 provides security mechanisms to keep each tenant's data separate unless the data is shared. If more than one MTS is used, they may be located in close proximity to one another (e.g., in a server farm located in a single building or campus), or they may be distributed at locations remote from one another (e.g., one or more servers located in city A and one or more servers located in city B). As used herein, each MTS could include logically and/or physically connected servers distributed locally or across one or more geographic locations. Additionally, the term "server" is meant to include a computing system, including processing hardware and process space(s), and an associated storage system and database application (e.g., OODBMS or RDBMS) as is well known in the art.

It should also be understood that "server system" and "server" are often used interchangeably herein. Similarly, the database object described herein can be implemented as single databases, a distributed database, a collection of distributed databases, a database with redundant online or offline backups or other redundancies, etc., and might include a distributed database or storage network and associated processing intelligence.

FIG. 10 also shows a block diagram of environment 910 further illustrating system 916 and various interconnections, in accordance with some implementations. FIG. 10 shows that user system 912 may include processor system 912A, memory system 912B, input system 912C, and output system 912D. FIG. 10 shows network 914 and system 916. FIG. 10 also shows that system 916 may include tenant data storage 922, tenant data 923, system data storage 924, system data 925, User Interface (UI) 1030, Application Program Interface (API) 1032, PL/SOQL 1034, save routines 1036, application setup mechanism 1038, applications servers 1000₁-1000N, system process space 1002, tenant process spaces 1004, tenant management process space 1010, tenant storage area 1012, user storage 1014, and application metadata 1016. In other implementations, environment 910 may not have the same elements as those listed above and/or may have other elements instead of, or in addition to, those listed above.

User system 912, network 914, system 916, tenant data storage 922, and system data storage 924 were discussed above in FIG. 9. Regarding user system 912, processor system 912A may be any combination of processors. Memory system 912B may be any combination of one or more memory devices, short term, and/or long term memory. Input system 912C may be any combination of input devices, such as keyboards, mice, trackballs, scanners, cameras, and/or interfaces to networks. Output system 912D may be any combination of output devices, such as monitors, printers, and/or interfaces to networks. As shown by FIG. 10, system 916 may include a network interface 920 (of FIG. 9) implemented as a set of HTTP application servers 1000, an application platform 918, tenant data storage 922, and system data storage 924. Also shown is system process space 1002, including individual tenant process spaces 1004 and a tenant management process space 1010. Each application server 1000 may be configured to tenant data storage 922 and the tenant data 923 therein, and system data storage 924 and the system data 925 therein to serve requests of user systems 912. The tenant data 923 might be divided into individual tenant storage areas 1012, which can be either a physical arrangement and/or a logical arrangement of data. Within each tenant storage area 1012, user storage 1014 and application metadata 1016 might be similarly allocated for each user. For example, a copy of a user's most recently used (MRU) items might be stored to user storage 1014. Similarly, a copy of MRU items for an entire organization that is a tenant might be stored to tenant storage area 1012. A UI 1030 provides a user interface and an API 1032 provides an application programmer interface to system 916 resident processes to users and/or developers at user systems 912. The tenant data and the system data may be stored in various databases, such as Oracle™ databases.

Application platform 918 includes an application setup mechanism 1038 that supports application developers' creation and management of applications, which may be saved as metadata into tenant data storage 922 by save routines 1036 for execution by subscribers as tenant process spaces 1004 managed by tenant management process 1010 for example. Invocations to such applications may be coded using PL/SOQL 34 that provides a programming language style interface extension to API 1032. A detailed description of some PL/SOQL language implementations is discussed in commonly assigned U.S. Pat. No. 7,730,478, titled METHOD AND SYSTEM FOR ALLOWING ACCESS TO DEVELOPED APPLICATIONS VIA A MULTI-TENANT ON-DEMAND DATABASE SERVICE, by Craig Weissman, filed Sep. 21, 2007, which is hereby incorporated by reference in its entirety and for all purposes. Invocations to applications may be detected by system processes, which manage retrieving application metadata 1016 for the subscriber making the invocation and executing the metadata as an application in a virtual machine.

Each application server 1000 may be communicably coupled to database systems, e.g., having access to system data 925 and tenant data 923, via a different network connection. For example, one application server 10001 might be coupled via the network 914 (e.g., the Internet), another application server 1000N−1 might be coupled via a direct network link, and another application server 1000N might be coupled by yet a different network connection. Transfer Control Protocol and Internet Protocol (TCP/IP) are typical protocols for communicating between application servers 1000 and the database system. However, other transport protocols may be used to optimize the system depending on the network interconnect used.

In certain implementations, each application server 1000 is configured to handle requests for any user associated with any organization that is a tenant. Because it is desirable to be able to add and remove application servers from the server pool at any time for any reason, there is preferably no server affinity for a user and/or organization to a specific application server 1000. In some implementations, therefore, an interface system implementing a load balancing function (e.g., an F5 Big-IP load balancer) is communicably coupled between the application servers 1000 and the user systems 912 to distribute requests to the application servers 1000. In some implementations, the load balancer uses a least connections algorithm to route user requests to the application servers 1000. Other examples of load balancing algorithms, such as round robin and observed response time, also can be used. For example, in certain implementations, three consecutive requests from the same user could hit three different application servers 1000, and three requests from different users could hit the same application server 1000. In this manner, system 916 is multi-tenant, wherein system 916 handles storage of, and access to, different objects, data and applications across disparate users and organizations.

As an example of storage, one tenant might be a company that employs a sales force where each call center agent uses system 916 to manage their sales process. Thus, a user might maintain contact data, leads data, customer follow-up data, performance data, goals and progress data, etc., all applicable to that user's personal sales process (e.g., in tenant data storage 922). In an example of a MTS arrangement, since all of the data and the applications to access, view, modify, report, transmit, calculate, etc., can be maintained and accessed by a user system having nothing more than network access, the user can manage his or her sales efforts and cycles from any of many different user systems. For example, if a call center agent is visiting a customer and the customer has Internet access in their lobby, the call center agent can obtain critical updates as to that customer while waiting for the customer to arrive in the lobby.

While each user's data might be separate from other users' data regardless of the employers of each user, some data might be organization-wide data shared or accessible by a plurality of users or all of the users for a given organization that is a tenant. Thus, there might be some data structures managed by system 916 that are allocated at the tenant level while other data structures might be managed at the user level. Because an MTS might support multiple tenants including possible competitors, the MTS should have security protocols that keep data, applications, and application use separate. Also, because many tenants may opt for access to an MTS rather than maintain their own system, redundancy, up-time, and backup are additional functions that may be implemented in the MTS. In addition to user-specific data and tenant specific data, system 916 might also maintain system level data usable by multiple tenants or other data. Such system level data might include industry reports, news, postings, and the like that are sharable among tenants.

In certain implementations, user systems 912 (which may be client machines/systems) communicate with application servers 1000 to request and update system-level and tenant-level data from system 916 that may require sending one or more queries to tenant data storage 922 and/or system data storage 924. System 916 (e.g., an application server 1000 in system 916) automatically generates one or more SQL statements (e.g., SQL queries) that are designed to access the desired information. System data storage 924 may generate query plans to access the requested data from the database.

Each database can generally be viewed as a collection of objects, such as a set of logical tables, containing data fitted into predefined categories. A "table" is one representation of a data object and may be used herein to simplify the conceptual description of objects and custom objects according to some implementations. It should be understood that "table" and "object" may be used interchangeably herein. Each table generally contains one or more data categories logically arranged as columns or fields in a viewable schema. Each row or record of a table contains an instance of data for each category defined by the fields. For example, a CRM database may include a table that describes a customer with fields for basic contact information such as name, address, phone number, fax number, etc. Another table might describe a purchase order, including fields for information such as customer, product, sale price, date, etc. In some multi-tenant database systems, standard entity tables might be provided for use by all tenants. For CRM database applications, such standard entities might include tables for account, contact, lead, and opportunity data, each containing pre-defined fields. It should be understood that the word "entity" may also be used interchangeably herein with "object" and "table".

In some multi-tenant database systems, tenants may be allowed to create and store custom objects, or they may be allowed to customize standard entities or objects, for example by creating custom fields for standard objects, including custom index fields. U.S. Pat. No. 7,779,039, titled CUSTOM ENTITIES AND FIELDS IN A MULTI-TENANT DATABASE SYSTEM, by Weissman, et al., and which is hereby incorporated by reference in its entirety and for all purposes, teaches systems and methods for creating custom objects as well as customizing standard objects in a multi-tenant database system. In some implementations, for example, all custom entity data rows are stored in a single multi-tenant physical table, which may contain multiple logical tables per organization. In some implementations, multiple "tables" for a single customer may actually be stored in one large table and/or in the same table as the data of other customers.

These and other aspects of the disclosure may be implemented by various types of hardware, software, firmware, etc. For example, some features of the disclosure may be implemented, at least in part, by machine-program product that include program instructions, state information, etc., for performing various operations described herein. Examples of program instructions include both machine code, such as produced by a compiler, and files containing higher-level code that may be executed by the computer using an interpreter. Examples of machine-program product include, but are not limited to, magnetic media such as hard disks, floppy disks, and magnetic tape; optical media such as CD-ROM disks; magneto-optical media; and hardware devices that are specially configured to store and perform program instructions, such as read-only memory devices ("ROM") and random access memory ("RAM").

While one or more implementations and techniques are described with reference to an implementation in which a service cloud console is implemented in a system having an application server providing a front end for an on-demand database service capable of supporting multiple tenants, the one or more implementations and techniques are not limited to multi-tenant databases nor deployment on application servers. Implementations may be practiced using other database architectures, i.e., ORACLE®, DB2® by IBM and the like without departing from the scope of the implementations claimed.

Any of the above implementations may be used alone or together with one another in any combination. Although various implementations may have been motivated by various deficiencies with the prior art, which may be discussed or alluded to in one or more places in the specification, the implementations do not necessarily address any of these deficiencies. In other words, different implementations may address different deficiencies that may be discussed in the specification. Some implementations may only partially address some deficiencies or just one deficiency that may be discussed in the specification, and some implementations may not address any of these deficiencies.

While various implementations have been described herein, it should be understood that they have been presented by way of example only, and not limitation. Thus, the breadth and scope of the present application should not be limited by any of the implementations described herein but should be defined only in accordance with the following and later-submitted claims and their equivalents.

What is claimed is:

1. A system comprising:
a database system implemented using a server computing system comprising a plurality of batch servers configurable to implement batch job processing comprising:
configuring, by the server computing system, a variable batch size according to a detected one of a range of reopening phases associated with a shared health event to process batches of patient records stored in a database associated with the database system, each reopening phase having a respective one of a range of restrictions on patient location;
for each batch of the patient records:
performing load balancing for the plurality of batch servers to process the batch of patient records using an interface system implementing the load balancing, the interface system being communicably coupled with the plurality of batch servers, the load balancing including analyzing and forwarding traffic to distribute workload among the plurality of batch servers;
obtaining, from a database, by the server computing system, data identifying a plurality of cancelled health-related appointments for the batch of patient records, the cancelled health-related appointments associated with the shared health event;
associating, by the server computing system, each of the patient records of the batch with a risk category from a plurality of risk categories ranging from a lowest risk to a highest risk, wherein a risk category is determined based at least on a treatment associated with a cancelled health-related appointment;
communicating, by the server computing system, with a client computing device associated with a patient having a cancelled health-related appointment to schedule a return appointment based at least on the detected reopening phase and on a risk category associated with a patient record of the patient, the communicating including receiving, by the server computing system, current health condition information of the patient;
based at least on the current health condition information of the patient showing symptoms consistent with symptoms associated with the shared health event, identifying, by the server computing system, the patient as a potential infected patient; and
performing, by the server computing system, contact tracing based at least on people that the patient has been in contact with while experiencing the symptoms.

2. The system of claim 1, the batch job processing further comprising:

receiving, by the server computing system, health history information of the patient from an electronic medical record associated with the patient; and generating, by the server computing system, a quarantine recommendation for the patient based on the health history information of the patient and based on the patient being identified as the potential infected patient.

3. The system of claim 2, wherein the quarantine recommendation for the patient is a quarantine at a healthcare facility when the health history information of the patient includes a risk factor identified by a health organization or a self-quarantine when the health history information of the patient does not include a risk factor identified by the health organization.

4. The system of claim 1, the batch job processing further comprising:

obtaining, from the database, by the server computing system, data identifying a plurality of healthcare facilities and resources available at each of the healthcare facilities; and selecting, by the server computing system, a healthcare facility from the plurality of healthcare facilities that has available resources required for quarantining the patient.

5. The system of claim 1, wherein the people that the patient has been in contact with while experiencing the symptoms is determined from one or more of family contacts, employment contacts or social contacts.

6. The system of claim 1, the batch job processing further comprising:

performing, by the server computing system, contact tracing based on geographical areas that the patient is associated with while experiencing the symptoms.

7. The system of claim 6, where the geographical areas that the patient is associated with while experiencing the symptoms are determined from global position system (GPS) locations recorded by the client computing device associated with the patient.

8. A computer program product comprising a non-transitory computer-readable medium storing computer-readable program code to be executed by one or more processors, the program code including instructions to implement batch job processing by a plurality of batch servers of a server computing system to:

configure a variable batch size according to a detected one of a range of reopening phases associated with a shared health event to process batches of patient records stored in a database, each reopening phase having a respective one of a range of restrictions on patient location;

for each batch of the patient records:

perform load balancing for the plurality of batch servers to process the batch of patient records using an interface system implementing the load balancing, the interface system being communicably coupled with the plurality of batch servers, the load balancing including analyzing and forwarding traffic to distribute workload among the plurality of batch servers;

obtain, from a database, data identifying a plurality of cancelled health-related appointments for the batch of patient records, the cancelled health-related appointments associated with the shared health event;

associate each of the patient records of the batch with a risk category from a plurality of risk categories ranging from a lowest risk to a highest risk, wherein a risk category is determined based at least on a treatment associated with a cancelled health-related appointment;

communicate with a client computing device associated with a patient having a cancelled health-related appointment to schedule a return appointment based at least on the detected reopening phase and on a risk category associated with a patient record of the patient, the communicating including receiving current health condition information of the patient;

based at least on the current health condition information of the patient showing symptoms consistent with symptoms associated with the shared health event, identify the patient as a potential infected patient; and perform contact tracing based at least on people that the patient has been in contact with while experiencing the symptoms.

9. The computer program product of claim 8, the program code further including instructions to:

receive health history information of the patient from an electronic medical record associated with the patient; and generate a quarantine recommendation for the patient based on the health history information of the patient and based on the patient being identified as the potential infected patient.

10. The computer program product of claim 9, wherein the quarantine recommendation for the patient is a quarantine at a healthcare facility when the health history information of the patient includes a risk factor identified by a health organization or a self-quarantine when the health history information of the patient does not include a risk factor identified by the health organization.

11. The computer program product of claim 8, the program code further including instructions to:

obtain, from the database, data identifying a plurality of healthcare facilities and resources available at each of the healthcare facilities; and select a healthcare facility from the plurality of healthcare facilities that has available resources required for quarantining the patient.

12. The computer program product of claim 8, wherein the people that the patient has been in contact with while experiencing the symptoms is determined from one or more of family contacts, employment contacts or social contacts.

13. The computer program product of claim 8, the program code further including instructions to:

perform contact tracing based on geographical areas that the patient is associated with while experiencing the symptoms.

14. The computer program product of claim 13, where the geographical areas that the patient is associated with while experiencing the symptoms are determined from global position system (GPS) locations recorded by the client computing device associated with the patient.

15. A computer-implemented method for performing contact tracing associated with a shared health event, the method comprising:

performing batch job processing by a plurality of batch servers of a server computing system, the batch job processing comprising:

configuring, by the server computing system, a variable batch size according to a detected one of a range of reopening phases associated with a shared health event to process batches of patient records stored in a database, each reopening phase having a respective one of a range of restrictions on patient location;

for each batch of the patient records:
- performing load balancing for the plurality of batch servers to process the batch of patient records using an interface system implementing the load balancing, the interface system being communicably coupled with the plurality of batch servers, the load balancing including analyzing and forwarding traffic to distribute workload among the plurality of batch servers;
- obtaining, from a database, by the server computing system, data identifying a plurality of cancelled health-related appointments for the batch of patient records, the cancelled health-related appointments associated with the shared health event;
- associating, by the server computing system, each of the patient records of the batch with a risk category from a plurality of risk categories ranging from a lowest risk to a highest risk, wherein a risk category is determined based at least on a treatment associated with a cancelled health-related appointment;
- communicating, by the server computing system, with a client computing device associated with a patient having a cancelled health-related appointment to schedule a return appointment based at least on the detected reopening phase and on a risk category associated with a patient record of the patient, the communicating including receiving, by the server computing system, current health condition information of the patient;
- based at least on the current health condition information of the patient showing symptoms consistent with symptoms associated with the shared health event, identifying, by the server computing system, the patient as a potential infected patient; and
- performing, by the server computing system, contact tracing based at least on people that the patient has been in contact with while experiencing the symptoms.

16. The method of claim 15, further comprising:
- receiving, by the server computing system, health history information of the patient from an electronic medical record associated with the patient; and
- generating, by the server computing system, a quarantine recommendation for the patient based on the health history information of the patient and based on the patient being identified as the potential infected patient.

17. The method of claim 16, wherein the quarantine recommendation for the patient is a quarantine at a healthcare facility when the health history information of the patient includes a risk factor identified by a health organization or a self-quarantine when the health history information of the patient does not include a risk factor identified by the health organization.

18. The method of claim 15, further comprising:
- obtaining, from the database, by the server computing system, data identifying a plurality of healthcare facilities and resources available at each of the healthcare facilities; and
- selecting, by the server computing system, a healthcare facility from the plurality of healthcare facilities that has available resources required for quarantining the patient.

19. The method of claim 15, wherein the people that the patient has been in contact with while experiencing the symptoms is determined from one or more of family contacts, employment contacts or social contacts.

20. The method of claim 15, further comprising:
- performing, by the server computing system, contact tracing based on geographical areas that the patient is associated with while experiencing the symptoms.

21. The method of claim 20, where the geographical areas that the patient is associated with while experiencing the symptoms are determined from global position system (GPS) locations recorded by the client computing device associated with the patient.

* * * * *